(12) United States Patent
Davey et al.

(10) Patent No.: US 7,368,232 B2
(45) Date of Patent: *May 6, 2008

(54) HIGH-THROUGHPUT ASSAY FOR VIRUS ENTRY AND DRUG SCREENING

(75) Inventors: Robert A. Davey, Galveston, TX (US); Andrey Kolokoltsov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/036,568

(22) Filed: Jan. 14, 2005

(65) Prior Publication Data

US 2005/0164171 A1 Jul. 28, 2005

Related U.S. Application Data

(63) Continuation-in-part of application No. 10/813,383, filed on Mar. 30, 2004.

(60) Provisional application No. 60/459,531, filed on Mar. 31, 2003, now abandoned.

(51) Int. Cl.
*C12Q 1/70* (2006.01)
(52) U.S. Cl. .................... 435/5; 435/8; 435/29; 435/32
(58) Field of Classification Search ............... 514/44, 514/13, 1, 241; 435/5; 424/188.1, 212.1, 424/209.1, 211.1, 144.1, 208.1, 85.1
See application file for complete search history.

(56) References Cited

U.S. PATENT DOCUMENTS

2004/0096823 A1 * 5/2004 Greene et al. .................. 435/5

FOREIGN PATENT DOCUMENTS

WO WO 02094874 A2 * 11/2002

OTHER PUBLICATIONS

Fields, Virology, 3rd Edition, p. 2722 (1996).*

Cleveland et al., "A region of the C-terminal tail of the gp41 envelope glycoprotein of human immunodeficiency virus type 1 contains a neutralizing epitope: evidence for its exposure on the surface of the virion," Journal of General Virology, 84, pp. 591-602 (2003).*
Aiken, "Pseudotyping Human Immunodeficiency Virus Type 1 (HIV-1) by the Glycoprotein of Vesicular Stomatitis Virus Targets HIV-1 Entry to an Endocytic Pathway and Suppresses bothe the requirement for Nef and the sensitivity to Cyclosporin A," Journal of Virology, vol. 71, No. 8, pp. 5871-5877 (1997).*
Card et al., "Pseudorabies Virus Envelope Glycoprotein gl Influences both Neurotropism and Virulence during Infection of the Rat Visual system," Journal of Virology, vol. 6, No. 5, pp. 3032-3041 (1992).*
Davis et al., "Comparison of High Throughput Screening Technologies for Luminescence Cell-Based Reporter Screens," Journal of Biomolecular Screening, vol. 7, No. 1, pp. 67-77 (2002).*
He et al., "Use of a Novel Human Immunodeficiency Virus Type 1 Reporter Virus Expressing Human Placentel Alkaline Phosphatase to Detect an Alternative Viral Receptor," Journal of Virology, vol. 69, No. 7, pp. 4587-4592 (1995).*
Kovacs et al., "Firefly luciferase as a marker for herpesvirus (pseudorabies virus) replication in vitro and in vivo," Journal of General Virology, 72, pp. 2999-3008 (1991).*
Jons et al., "Green fluorescent protein expressed by recombinant pseudorabies virus as an in vivo marker for viral replication," Journal of Virological Methods 66, pp. 283-292 (1997).*
Pomeranz et al, Molecular Biology of Pseudorabies Virus: Impact on Neurovirology and Veterinary Medicine, vol. 69, No. 3, pp. 462-500 (2005).*

* cited by examiner

*Primary Examiner*—Mary E. Mosher
(74) *Attorney, Agent, or Firm*—Benjamin Aaron Adler

(57) ABSTRACT

The present invention provides a rapid virus entry/binding detection assay. An enzyme such as luciferase was incorporated at the C-terminal end of viral envelope proteins of the HIV Nef protein that would specifically associate with cell membranes to deliver the enzyme into viral particles upon viral assembly. Virus entry/binding can then be assayed by determining the enzymatic activities in infected cells. The assay allows high-throughput non-radioactive detection of virus entry within 30 minutes after virus-cell contact. This assay provides high signal to noise ratio and is useful for screening compounds that affect virus-cell binding and entry. The design also permits packaging of potential therapeutic proteins into functional virus particles and delivering them to specific cellular targets.

13 Claims, 15 Drawing Sheets

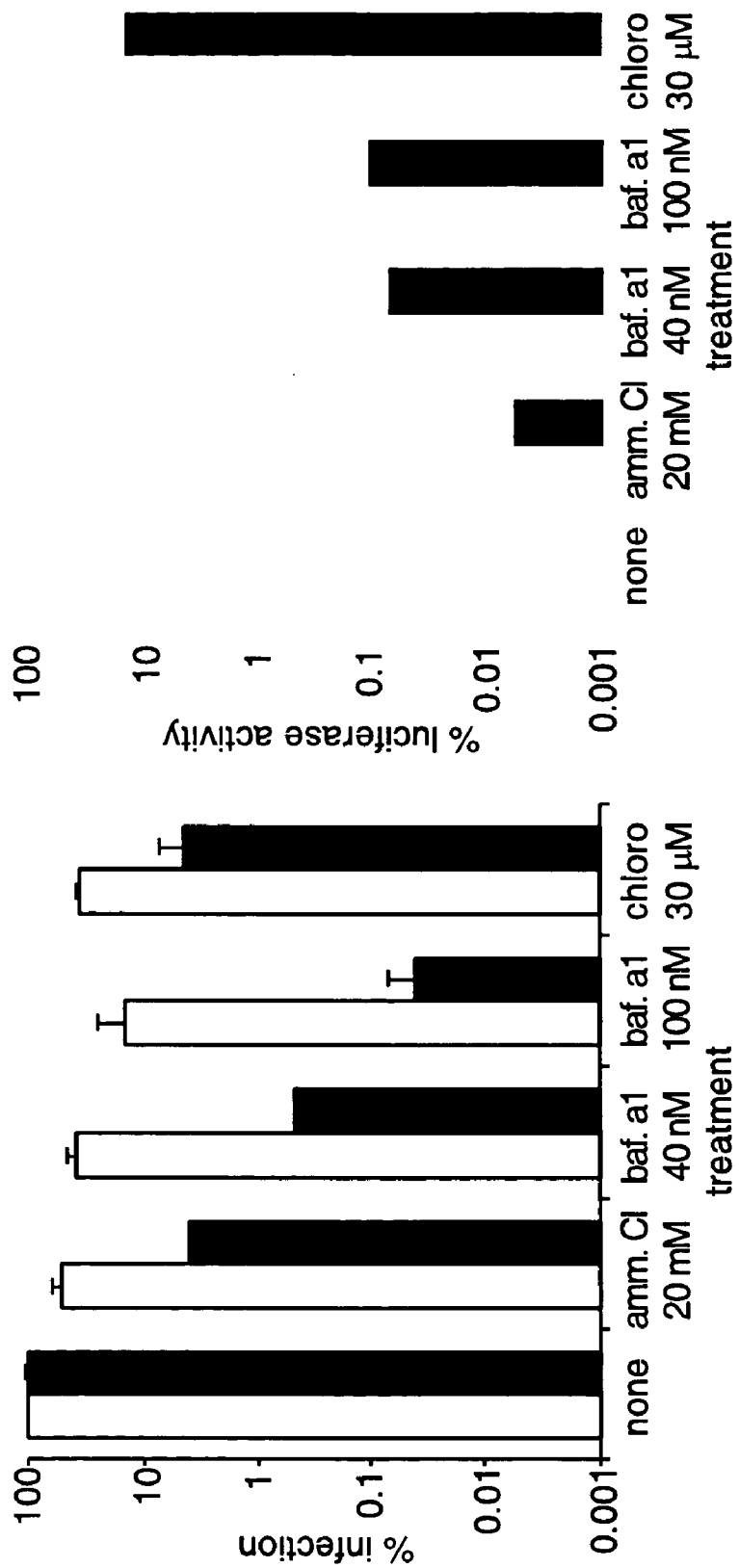

SEQUENCE LISTING

<160> NUMBER OF SEQ ID NOS: 8

<210> SEQ ID NO 1
<211> LENGTH: 30
<212> TYPE: DNA
<213> ORGANISM: artificial sequence
<220> FEATURE:
<221> NAME/KEY: primer_bind
<223> OTHER INFORMATION: Oligonucleotide sequence to modify 3' end
      of Friend57 MLV envelope gene to replace
      a native stop codon with EcoRV or EcoRI
      restriction endonuclease site.

<400> SEQUENCE: 1
ccatcgatta gttcaatttg ttaaagacag                              30

<210> SEQ ID NO 2
<211> LENGTH: 35
<212> TYPE: DNA
<213> ORGANISM: artificial sequence
<220> FEATURE:

```
<221> NAME/KEY: primer_bind
<223> OTHER INFORMATION: Oligonucleotide sequence to modify 3' end
      of Friend57 MLV envelope gene to replace
      a native stop codon with EcoRV or EcoRI
      restriction endonuclease site.

<400> SEQUENCE: 2
gatcgaattc tggctcgtat tctagtggtt ttagc                              35

<210> SEQ ID NO 3
<211> LENGTH: 35
<212> TYPE: DNA
<213> ORGANISM: artificial sequence
<220> FEATURE:
<221> NAME/KEY: primer_bind
<223> OTHER INFORMATION: Oligonucleotide sequence to modify firefly
      luciferase gene to gain EcoRV or EcoRI
      restriction endonuclease site at its 5' end.

<400> SEQUENCE: 3
gatcgaattc gaagacgcca aaaacataaa gaaag                              35

<210> SEQ ID NO 4
<211> LENGTH: 35
<212> TYPE: DNA
<213> ORGANISM: artificial sequence
<220> FEATURE:
<221> NAME/KEY: primer_bind
<223> OTHER INFORMATION: Oligonucleotide sequence to modify firefly
      luciferase gene to gain EcoRV or EcoRI site
      at its 5' end and two tandem stop codons
      and NotI site at its 3' end.

<400> SEQUENCE: 4
gatgcggccg cttacacggc gatctttccg ccctt                              35

<210> SEQ ID NO 5
<211> LENGTH: 4
<212> TYPE: PRT
<213> ORGANISM: artificial sequence
<220> FEATURE:
<223> OTHER INFORMATION: 4 amino acid residue in the spacer
      peptide between the envelope protein C-
      terminus and the luciferase N-terminus
      in env-luc2 construct.

<400> SEQUENCE: 5

Glu Phe Gly Ser

<210> SEQ ID NO 6
<211> LENGTH: 32
<212> TYPE: DNA
<213> ORGANISM: artificial sequence
<220> FEATURE:
<221> NAME/KEY: primer_bind
<223> OTHER INFORMATION: Sense strand oligonucleotide sequence for the
      T471P mutation.

<400> SEQUENCE: 6
cgccgcggga gttagggccc ggaactaccg cc                                 32

<210> SEQ ID NO 7
<211> LENGTH: 29
<212> TYPE: DNA
<213> ORGANISM: artificial sequence
<220> FEATURE:
<221> NAME/KEY: primer_bind
<223> OTHER INFORMATION: oligonucleotide sequence for the
      Nef encoding region
```

-continued

```
<400> SEQUENCE: 7
atggatccat gggcggcaag tggagcaag                                      29

<210> SEQ ID NO 8
<211> LENGTH: 29
<212> TYPE: DNA
<213> ORGANISM: artificial sequence
<220> FEATURE:
<221> NAME/KEY: primer_bind
<223> OTHER INFORMATION: oligonucleotide sequence for the
      Nef encoding region

<400> SEQUENCE: 8
tagaattcgc agtccttgta gtactcggg                                      29
```

HIGH-THROUGHPUT ASSAY FOR VIRUS ENTRY AND DRUG SCREENING

CROSS REFERENCE TO RELATED APPLICATION

This is a continuation-in-part application of patent application U.S. Ser. No. 10/813,383, filed on Mar. 30, 2004, which claims benefit of priority of provisional application U.S. Ser. No. 60/459,531, filed on Mar. 31, 2003, now abandoned.

Federal Funding Legend

This invention was produced using funds obtained through a National Institute of Allergy and Infectious Diseases (NIAID) grant U54 AI057156. Consequently, the Federal government has certain rights in this invention.

BACKGROUND OF THE INVENTION

1. Field of the Invention

The present invention relates generally to the field of virology. More specifically, the present invention provides assays that measure virus binding and entry into target cells.

2. Description of the Related Art pH-dependent models such as influenza A and semliki forest virus have been used to study the mechanisms of enveloped virus entry because it is possible to induce en-masse fusion event by dropping the pH of the medium. Fluorescence dequenching or FRET assays are used to measure the kinetics of fusion in such viruses and have been used to understand the effects of mutations and anti-viral drugs. In this assay, fluorescent probes incorporated in the virus membranes mix with and become diluted in the target cell or liposome membrane. The resulting change in fluorescence gives a real-time measure of fusion. These entry assays cannot be applied easily to pH-independent viruses since fusion events are infrequent, cannot be coordinated and the receptors are difficult to manipulate since they tend to be integral, multi-transmembrane span-containing proteins. In such studies, passive diffusion of fluorophore contributes significantly to the signal and complex analysis of the data is required to observe signal due to fusion.

The need for more sensitive measurement of pH-dependent virus entry has led to the development of assays to detect cell-cell fusion, early genome replication events and assays that use recombinant viral protein-GFP fusions. In assays detecting cell-cell fusion, which is used to confirm the role of factors important in fusion, cells made to express virus envelope proteins on the surfaces are labeled with one fluorophore and mixed with target cells bearing receptor and second fluorophore. Fusion is measured by observing syncytia formation. Independent labeling of cell membrane and cytoplasm provides information on membrane and cytoplasm mixing. It has been shown that syncytia formation is slow and does not correlate to infection kinetics. Additionally, in case of HIV, the chemokine receptor, Bonzo promotes syncytia but does not play any significant role in entry.

There are several assays that detect virus infection. Some assays measure infection by using reporter gene expression in the infected cell. This is a very complicated process. To obtain expression, a virus must penetrate the cell membrane, the core must be trafficked to the correct subcellular location, then the genome is exposed and finally the reporter is expressed. This requires, for example in retroviruses, the cell to be at a specific stage and the gene expression requires at least 24 hours after contact with cells which is far removed from the initial entry event.

Other assays, which involve making virus-protein fusions to green fluorescent protein, have been useful to follow virus after it has entered the cell. The use of fluorescently labeled dUTP even permits visualization of genomes undergoing reverse transcription. These assays cannot be easily used to examine virus entry as cell bound viruses cannot be differentiated from those which have just entered the cells. For retroviruses, particle to infectious particle ratios typically exceed 10-100. This means that most viruses are either defective or trafficked to non-productive pathways within the cell.

Contents-mixing assays, which measure release of virus contents into the cell or target vesicle, demonstrate great potential for rapid measurement of virus entry. In case of retroviruses, it takes advantage of the fact that viral cDNA synthesis is limited by access to deoxyribonucleotides. When the viral genome is exposed by capsid disassembly after entry, dNTPs can access the viral polymerase and synthesis proceeds. Transcripts can then be detected by PCR, typically around 4 hours after cell contact. It is not known at what point within this 4-hour window the genome uncoating take place nor is it known when the dNTP pool is contacted.

A method where enzyme β-lactamase is fused to HIV protein vpr was developed recently to obtain quantitative data. Vpr is packaged into HIV particles as part of virus assembly and provides a means of targeting a marker enzyme into the particle. Caged substrate was perfused into cells to give signal. Detection of entry required 12 hours of cell culture for production of sufficient reaction product. To enable shorter measurement times, an MOI of more than 10-100, which is not physiological, is required.

A few virus entry inhibitors exist for influenza and HIV. While these inhibitors show some promise, they are far from perfect and have low efficacy. Discovery of similar but more effective drugs has been hindered by a lack of high-throughput, high signal to noise assay for screening lead compounds/drugs. Thus, the prior art is deficient in assays that are fast, simple, physiological and sensitive to measure virus entry. The present invention fulfils this need by providing methods that allow rapid and high-throughput non-radioactive detection of virus entry.

SUMMARY OF THE INVENTION

The present invention allows rapid and high-throughput non-radioactive detection of virus entry. The method provides a signal to noise ratio of >100-1000 and can detect both pH-dependent and independent virus entry into cells within 30 minutes after virus-cell contact.

In one embodiment of the present invention, there is provided a method of detecting virus binding and entry to target cell comprising the steps of creating an envelope-enzyme fusion protein by attaching an enzyme to the C-terminal end of a viral envelope protein. Virus particles comprising of the fusion protein and wild type envelope protein are generated and infect target cells. Activities of enzyme measured in such infected cells are measures of virus binding and entry to the target cells that are mediated by the wild type viral envelope protein.

Generally, the wild type viral envelope protein can be derived from viruses such as murine leukemia virus, human immunodeficiency virus, retrovirus, Vesicular Stomatitis virus, Arenaviruses, Hanta virus, Ebola virus and Venezuelan Equine Encephalitis virus. Preferably, the envelope-enzyme fusion protein comprises envelope protein of Murine leukemia virus or HIV Nef protein. Examples of enzymes that can be used to generate the fusion protein include, but are not limited to, luciferase, bacterial or placental alkaline phosphatase, b-galactosidase, and fluorescent proteins such as Green fluorescent protein or toxins. The assay, in general, can also be carried out in 96-well plate.

In another embodiment, there is provided a method of evaluating the influence of amino acid substitution(s) on virus binding and entry comprising the steps of constructing a mutant containing the amino acid substitution(s) in a viral envelope protein, and creating an envelope-enzyme fusion protein by attaching an enzyme to the C-terminal end of a viral envelope protein. The creation of envelope-enzyme fusion protein, generation of virus particle comprising the mutant envelope protein and the fusion protein as well as infection of target cells is carried out in a manner as described herein. Measurement of enzyme activities in lysed and intact infected cells will enable evaluation of amino acid substitution(s) on virus binding and entry.

In still another embodiment, there is provided a method for determining whether the viral entry mechanism is pH dependent comprising all the same steps as described earlier. However, in this case, the enzyme activities are measured in the absence and presence of the inhibitors of endosomal acidification where decreased enzyme activities in the presence of the inhibitors indicate that the virus has a pH-dependent mode of entry.

In another embodiment, there is provided a method of receptor-dependent targeted delivery of a therapeutic protein. This method comprises the step of attaching a therapeutic protein to the C-terminal end of a viral envelope protein, thereby creating a fusion protein. Virus particles comprising the fusion protein and wild type viral envelope protein are then generated, wherein cell binding of the wild type viral envelope protein would mediate receptor-dependent targeted delivery.

The present invention also provides a pharmaceutical composition comprising therapeutic protein-containing virus described above. Preferably, the pharmaceutical composition comprises the novel active composition of the present invention and a pharmaceutically acceptable carrier.

In another embodiment, there is provided a kit comprising (a) enzyme-containing virus pseudotypes described herein and (b) substrate for that particular enzyme.

In yet another embodiment, there is provided a method for screening neutralizing antibodies in patients' sera. The creation of an envelope-enzyme fusion protein, generation of virus particles comprising the fusion protein and wild type viral envelope protein as well as infection of target cells in the presence of the patients' sera are carried out as described herein. Decreased enzyme activities in the presence of the sera indicate that there are neutralizing antibodies in the sera.

In still yet another embodiment of the present invention, there is provided a method of screening for a compound that inhibits virus binding and entry to target cell. The creation of an envelope-enzyme fusion protein, generation of virus particle comprising the fusion protein and wild type envelope protein as well as infection of target cells is carried out as described herein. Decreased enzyme activities in the presence of the compound indicate that the compound inhibits virus binding and entry to the target cells mediated by the wild type viral envelope protein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 7A shows the design of MLV envelope-luciferase fusion protein (env-luc) schematically where the open and closed arrowheads indicate native cleavage site by furin (at SU-TM junction) and viral proteases (at TM-p2e junction) respectively. FIG. 7B shows the western blots of lysates from cells transfected with plasmids encoding wild-type Friend MLV envelope (env) alone or with env-luc1 and env-luc2 constructs or expression vector pCDNA3 (control) alone and pelleted particles collected from the culture supernatants. Blots containing cells lysed in 1% NP-40 were probed with anti-Rauscher MLV (anti-env) antibody that cross-reacts with Friend MLV envelope protein. FIG. 7B (I, left panel) shows cell lysates and particles isolated by pelleting through a 20% sucrose cushion. FIG. 7B (II, right panel) shows lysate of cells transfected with plasmids encoding env (5 µg) or env+env-luc1 (4 and 1 µg respectively). The arrowhead indicates band of predicted size for env-luc fusion protein with size markers to the left. FIG. 7C shows optimization of virus production by varying the ratio of env-luc1 to wild type envelope protein and determining the luciferase activity (left axis) for intact (squares) and lysed (circles, 1% NP-40) particles. Virus titer (triangles, right axis) was determined by infecting 293-CAT cells in serial, five-fold dilutions and staining them for β-galactosidase after 2 days.

FIG. 10A-10B shows effect of endosomal acidification inhibitors on infection and luciferase entry-assay signal. Cells ($2 \times 10^6$ per sample) were treated with ammonium chloride (amm.Cl), bafilomycin a1 (baf. A1) or chloroquine (chloro) at 20 mM, 40 nM+100 nM and 30 µM, respectively, and then Friend MLV (open bars) or VSV-G (solid bars) pseudotyped virus encoding β-galactosidase and containing env-luc1 was applied. Half of the cells were plated and colonies counted after 2 days by staining for β-galactosidase activity (FIG. 10A, left panel). The remaining cells were assayed for luciferase activity (FIG. 10B, right panel) after 1 hour.

FIG. 17 shows the effect of endosomal acidification inhibitor on the entry of MLV env pseudotyped virus expressing HIV Nef-Luc fusion protein. Approximately $10^6$ 293-mCAT-1 cells were pre-incubated with or without bafilomycin (40 nM) for 1 h at 37° C. Subsequently, sucrose-purified MLV env pseudotyped virus particles were added and incubation continued for an additional hour. The cells were then washed and luciferase activity was measured.

FIG. 18 shows neutralization of MLV env pseudotyped virus entry by specific antibodies. HEK 293mCAT-1 cells were trypsinized and approx. $10^6$ cells were incubated with sucrose-purified MLV env pseudotyped virus, which was previously incubated with either anti-MLVgp70 antibody or anti-HIVgp120. Incubation was carried out for 3 h at 37° C. with continuous rotation. Subsequently, the cells were pelleted, washed with DMEM+10% FBS and resuspended in luciferin-containing buffer. Luciferase activity was measured 2 min. after the addition of buffer.

FIG. 19 shows entry kinetics of Ebola env pseudotyped virus expressing HIV Nef-Luc fusion protein. HEK293FT cells were trypsinized and approx. $10^6$ cells were incubated with sucrose-purified Ebola env pseudotyped virus for 1, 2 or 3 h. At the end of each incubation period, the cells were pelleted, washed once with DMEM+10% FBS and resuspended in luciferin-containing buffer. Luciferase activity was measured immediately after resuspension, and then at 1 min. intervals for 5 min.

FIG. 20 shows the effect of endosomal acidification inhibitors on entry of Ebola env pseudotyped virus. HEK 293FT cells were trypsinized and approx. $10^6$ cells were pretreated with $NH_4Cl$ (20 mM) or bafilomycin (40 nM) for 1 hour at 37° C. Control cells were treated with DMSO (carrier). Subsequently, sucrose-purified Ebola virus env pseudotyped virus were added to each sample and incubation continued for an additional 3 hours. Cells were then pelleted, washed once with DMEM+10% FBS and resuspended in luciferase buffer. Luciferase activity was measured 2 minutes after resuspension.

FIG. 21 shows neutralization of Ebola env pseudotyped virus entry by specific antibodies. HEK 293FT cells were trypsinized and approx. $10^6$ cells were incubated with sucrose purified Ebola virus pseudotype, which was previously incubated with either anti-anti-Ebola neutralizing antibody or anti-influenza neutralizing antibody (control). Incubation was carried out for 3 h at 37° C. with continuous rotation. Subsequently, the cells were pelleted, washed with DMEM+10% FBS and resuspended in luciferin-containing buffer. Luciferase activity was measured 2 min. after the addition of luciferase buffer.

FIG. 22 shows viral entry of HIV env pseudotyped virus comprising gp160 (HIV envelope protein) from HIV IIIB strain (CXCR4-specific strain). U87 glioblastoma cells were transfected with either CD4+CXCR4 (U87/CD4/X4) or CD4+CCR5 (U87/CD4/R5). A semi-confluent plate of each cell type was trypsinized and approx $8 \times 10^5$ cells of each type were incubated with sucrose-purified HIV IIIB-based env pseudotyped virus for 5 h at 37° C. with continuous rotation.

After the incubation, cells were pelleted, washed once with DMEM+10% FBS, and resuspended in luciferin-containing buffer. Luciferase activity was measured immediately after the addition of buffer, and then at 1 min. intervals for 5 min.

Figure 23:
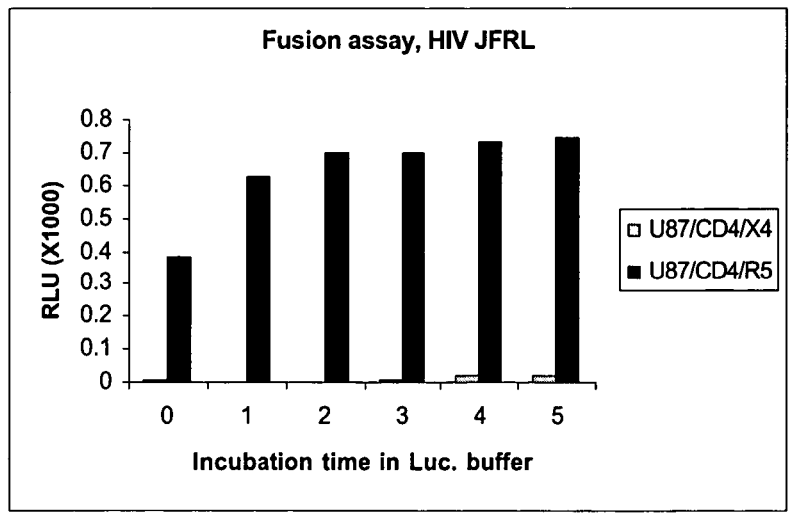

FIG. 23 shows viral entry of HIV env pseudotyped virus comprising gp160 (HIV envelope protein) from HIV JFRL strain (CCR5-tropic strain). The experiment was performed as that described in FIG. 22.

Figure 24:
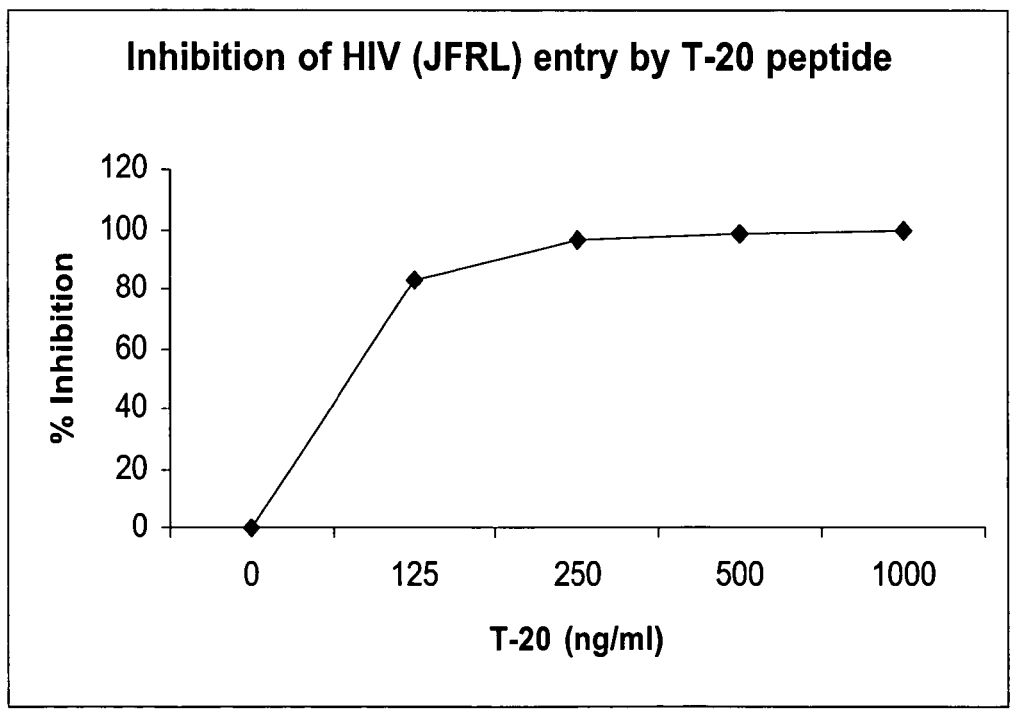

FIG. 24 shows inhibition of HIV-1 env pseudotyped virus entry by T-20 peptide (ENFURVITIDE), a previously characterized entry inhibitor specific for HIV strains. U87 cells bearing CD4 and CCR5 (U87/CD4/R5) were trypsinized and approx. $8 \times 10^5$ cells were incubated with T-20 peptide at various concentrations (0, 1000, 500, 250 and 125 ng/ml) for 1 h at 37° C. with continuous rotation. After incubation, the cells were pelleted and resuspended with purified HIV-JFRL envelope protein pseudotyped particles (0.2 ml). Each reaction was replenished with the same concentration of T-20 peptide as before. The tubes were incubated for an additional 5 h, followed by washing of cells with DMEM+10% FBS. The washed pellets were then resuspended in luciferin-containing buffer. Luciferase activity was measured 2 min. after the addition of buffer. Luciferase activity in T-20-treated samples was compared to that in untreated sample and % inhibition was determined.

DETAILED DESCRIPTION OF THE INVENTION

Figure 1:
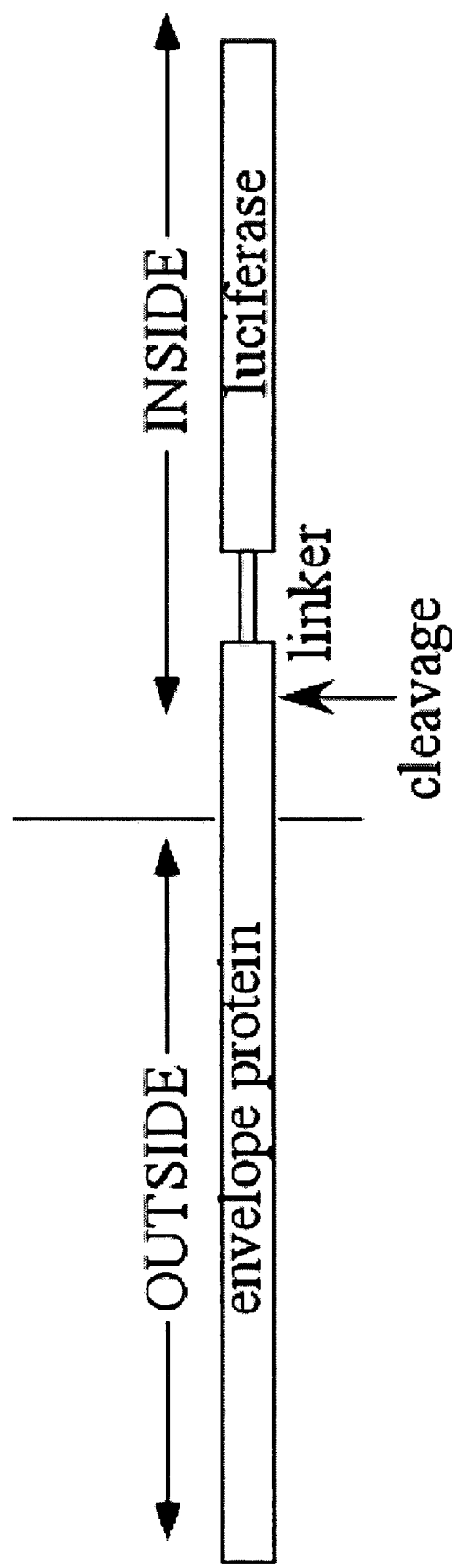
FIG. 1 shows envelope-luciferase construct.

In contrast to other assays that use a reporter gene, the assay of the present invention utilizes a reporter enzyme protein incorporated into the virus itself. In one embodiment, the virus envelope protein of a murine leukemia virus (MLV) was modified to have a luciferase enzyme attached at its C-terminus. FIG. 1 shows the envelope-luciferase construct. Once the construct is incorporated into virus, the envelope-luciferase construct is further processed by a viral protease (cleavage, FIG. 1). Consequently, the luciferase is released into the cytoplasm of the virus particle, thereby permitting easy assess and interaction with substrate.

In another embodiment, the reporter enzyme protein is attached to HIV Nef protein. This protein normally associates with the inner side of HIV virus membrane. Upon binding and entry of virus particles into target cells, the Nef-reporter enzyme fusion protein becomes exposed and enzymatic activities can then be measured. In general, proteins that are membrane associated and expressed on cell membrane where virus is assembled can be used to construct the reporter enzyme fusion protein.

While luciferase was used in this example, in practice any enzyme or protein could be attached in the same way. Examples of other enzymes or proteins include, but are not limited to, bacterial or placental alkaline phosphatase, b-galactosidase, fluorescent proteins such as green fluorescent protein or toxins.

The viral entry assay disclosed herein takes advantage of making pseudotyped viruses. Pseudotyped particles contain the core of one virus (e.g. murine leukemia virus core or HIV core) and envelope proteins of a donor virus. Since the receptor/cell specificity and entry characteristics are dictated by virus envelope proteins, receptor binding and entry characteristics of these pseudotyped particles mimic those of the donor virus.

Viruses are assembled by transfection of cells with wild-type envelope protein, the envelope-luciferase construct and plasmids encoding virus structural proteins. A marker gene distinct from luciferase may be incorporated as well, although this is not necessary for this assay. Virus is then purified from culture supernatants or crude medium can be used directly. Addition of virus-containing solutions to cells lacking virus receptor gives no enzyme activity in the presence of the substrate luciferin. In the presence of receptor positive cells, there was a dramatic increase in luciferase-associated activity within 15 minutes after incubation with virus particles. The signal was not diminished upon addition of EDTA, indicating that the envelope-luciferase construct had reached a compartment protected from EDTA and the virus must have been internalized or entered at the cell surface.

Generally, signals exceeding 3,000 light units/10 seconds were observed after a two-hour incubation with receptor positive cells. Strong signals can be detected after incubation for only 30 minutes. The assay can be performed in a 96-well plate using a luminometer capable of measuring this format. Signal:noise ratio was >1000 with background subtracted and >10 without subtracting noise in the instrument. Note that signal was easily detected within 15 minutes with a >1000-fold signal to noise ratio. This indicates that the assay can be used for high throughput drug screening.

Viruses expressing the murine leukemia virus (MLV) envelope protein would enter only mouse cells or cells made to express the murine receptor by DNA transfection. Normally, human cells do not support infection. However, since the envelope-luciferase component of the virus is only one fifth of the total envelope proteins expressed on the surface, it is possible to make other MLV pseudotypes that infect human cells. Viruses that can be pseudotyped onto MLV particles include HIV (and other retroviruses), vesicular stomatitis virus (VSV), Arenaviruses (Lassa Fever agent), Hanta viruses, Ebola and Venezuelan equine encephalitis virus among others. Similarly, pseudotype virus particles comprising HIV Nef-reporter enzyme fusion protein can be constructed. These viruses are natural agents of infectious disease and also potential bioterrorist agents. Therefore, this assay provides a rapid mechanism to screen for novel compounds that inhibit entry of these viruses as well.

The luciferase-based assay in the present invention was shown to measure specific adherence to cells and not non-specific breakdown of luciferase-containing particles since only receptor-bearing cells gave signal. In addition, the present invention also demonstrated that mutant containing T471P amino acid substitution in the fusion peptide of murine leukemia virus envelope protein gave no signal but bound to cells normally. This further indicated that the assay measures only the entry of virus and not other events following virus attachment such as endocytosis or non-specific degradation of the particles that might expose the luciferase. For these experiments, binding was determined by lysing the cells and measuring total luciferase activity. This unique feature of the assay that permitted evaluation of amino acid substitution for both virus-receptor interaction and entry in the same sample should also permit evaluation of influence of other amino acid substitutions on entry.

The assay disclosed herein gives an independent measure of virus entry kinetics for a retrovirus at MOI values of much less than 1. Under these conditions, signal could be detected between 5 and 20 minutes after cell contact and followed simple kinetics for over an hour. From analysis of pulse chase experiments a delay of approximately 15 minutes after virus binding to the cell occurred before significant fusion was seen. The importance of this delay remains unclear but is very similar to lags seen for HIV entry. It may represent the time required to form a fusion pore, deliver the luciferase into the cell cytoplasm and then access its substrates. This data is consistent with relatively slow formation of fusion pore seen for other enveloped viruses such as influenza A and vesicular stomatitis virus (VSV). The lag may also indicate cellular signaling, reorganization or trafficking events may be required for entry as suggested for HIV. These findings are consistent with a rapid mechanism of entry with similar kinetics to that seen for pH-dependent enveloped viruses such as influenza A and VSV.

In general, enveloped viruses can be divided into those with a pH-dependent or independent mechanism of entry. pH-dependent viruses require trafficking to acidified endosomal compartments. A block to infection by inhibitors of endosomal acidification has been used as evidence for pH dependence. However, the inhibitors used in such studies are typically cytotoxic and may affect stages of infection other than entry, such as uncoating and trafficking to cellular dNTP pool. Earlier reports had indicated that murine leukemia virus have both pH-dependent and pH-independent mechanisms of entry.

Since the luciferase-based assay disclosed herein is a rapid and quantitative measure of viral entry, it permits extensive dissection of virus entry pathway using inhibitors that are otherwise toxic to cells on prolonged exposure. In addition, the ability to produce vesicular stomatitis virus (VSV)-G pseudotype with similar luciferase activity to that of murine leukemia virus provided a control for these experiments and emphasized the flexibility of the assay system. The present invention demonstrated inhibitors of endosomal acidification inhibited signal from vesicular stomatitis virus pseudotypes but not murine leukemia virus, consistent with the pH-independent mode of entry for the later virus.

The effects on viral entry were examined on compounds such as chloroquine and ammonium chloride, which are weak bases that accumulate in and buffer the change in pH in endosome, as well as bafilomycin A1 which is specific inhibitor on the endosomal proton pump. Each compound only weakly affected the signal from Friend-murine leukemia virus (MLV) particles. However, they inhibited the signal observed with VSV-G pseudotype, which is known to have a pH-dependent mechanism of entry. A 1000 to 10,000-fold decrease in signal was observed in signal for VSV-G pseudotype in the presence of bafilomycin and ammonium chloride, compared to at most a 2-fold change for MLV. This assay not only confirmed previous report that MLV do not require endosomal acidification to trigger entry but also yielded a quantitative data with sensitivity far exceeded other previous assays. Thus, this assay can be used to study entry mechanisms and inhibitors.

Figure 7A:
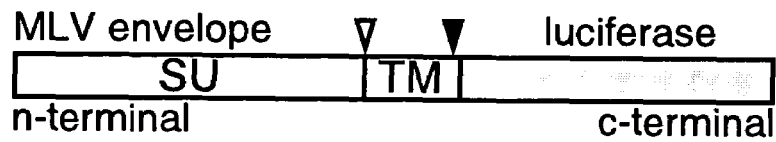
FIG. 7A-7C shows the design of the construct, production and optimization of MLV incorporating luciferase in the viral lumen.

The methods disclosed herein not only can be used to deliver luciferase to target cell, they can also be used to package other proteins which are useful in virus-mediated therapies and nanotechnology. Based on titration of recombinant luciferase (Quantilum, Promega) in buffer, it was possible to detect approximately 2,000 molecules. The inclusion of medium to harvest virus did not affect this number greatly. Based on virus titer that was $10^6$ infectious particles/ml with an activity ratio of approximately $10^5$ counts/sec/ml, the specific activity was 0.1 counts/sec/infectious particle. Therefore, assuming a particle/infectious-particle ratio of 10 to 100, even distribution of enzyme and efficient lysis of virus particles, there could be between 2 to 20 molecules of luciferase packaged per particle. The present invention demonstrated that the viral particles have a finite capacity for luciferase since attempts to increase the viral protein-enzyme fusion constructs (env-luc1) resulted in exposure of the enzyme to the suspension buffer and loss of virus titer (FIG. 7). This was consistent with the observation that env-luc1 construct, while produced at slightly higher levels than env-luc2 in cells, incorporated poorly into particles.

In comparison, env-luc2, which was incorporated well, produced particles that were permeable to luciferin. However, when the wild-type envelope and the env-luc1 construct were combined to make virus, titers were restored to normal with most virus being intact. Proteins of a similar size as luciferase (61 kDa) may also be tolerated. This design provides a simple system to package a therapeutic protein in functional virus particles, deliver it specifically to a target cell by efficient receptor-dependent targeting and have it released free of the virus into the cytoplasm of the target cell.

Luciferase-containing virus pseudotypes may also be useful for diagnostic assays. The present invention demonstrated efficiency in the making of VSV-G chimeric virus as well as ability of the assay to work in a 96-well format without difficulty, thus enabling it to be useful in making other virus pseudotypes and also being useful for diagnostic purposes. Rapid execution of the assay would reduce a 1-2 day diagnostic assay into several hours. This requires the envelope protein of the donor virus and the env-luc protein accumulate at the same locale to be incorporated into the same particle. Since the number of MLV pseudotypes that have been successfully produced is continually on the increase, the potential use for this assay will also expand.

Luciferase containing viruses may also permit visualization of entry events. With a sufficiently sensitive camera, it would be possible to detect production of light upon combination of the released luciferase and substrates. Others have shown that imaging of cells expressing luciferase is possible, but requires the use of image-intensifying cameras and exposure of the sample for tens of seconds. As camera sensitivity increases, this may be more practical.

In one embodiment, the present invention is directed to a method of detecting virus binding and entry to target cells. The method steps include attaching an enzyme to the C-terminal end of a viral envelope protein, thereby creating a envelope-enzyme fusion protein; generating virus particles comprising the envelope-enzyme fusion protein and wild type viral envelope protein; infecting target cells with the virus particles; and measuring enzyme activities in the infected cells, wherein such enzyme activities are measures of virus binding and entry to the target cells mediated by the wild type viral envelope protein.

Generally, the wild type viral envelope protein can be derived from viruses such as murine leukemia virus, human immunodeficiency virus, retrovirus, Vesicular Stomatitis virus, Arenaviruses, Hanta virus, Ebola virus and Venezuelan Equine Encephalitis virus. Preferably, the envelope-enzyme fusion protein comprises envelope protein of Murine leukemia virus or HIV Nef protein. Examples of enzymes that can be used to generate the fusion protein include, but are not limited to, luciferase, bacterial or placental alkaline phosphatase, b-galactosidase, and fluorescent proteins such as Green fluorescent protein or toxins. The assay, in general, can also be carried out in 96-well plate.

Figure 2:
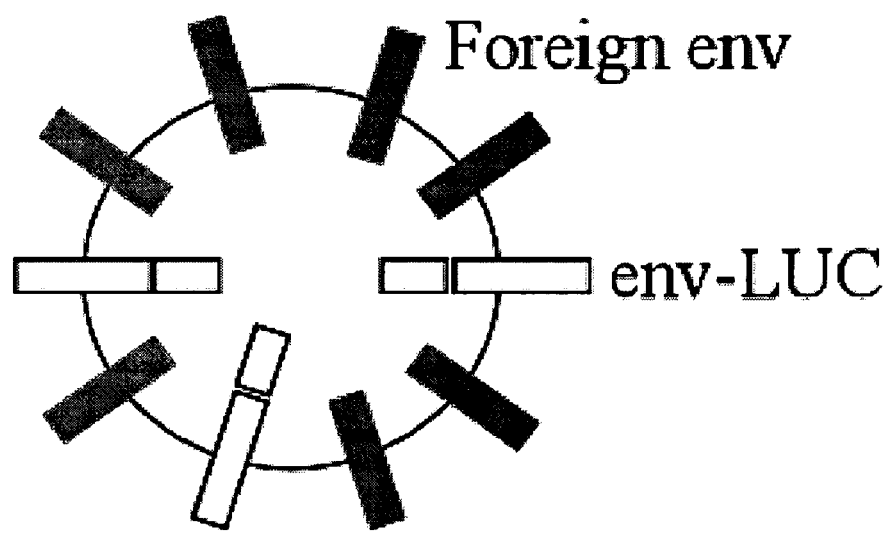
FIG. 2 shows mosaic virus containing foreign envelope proteins and envelope-luciferase construct.
Figure 3:
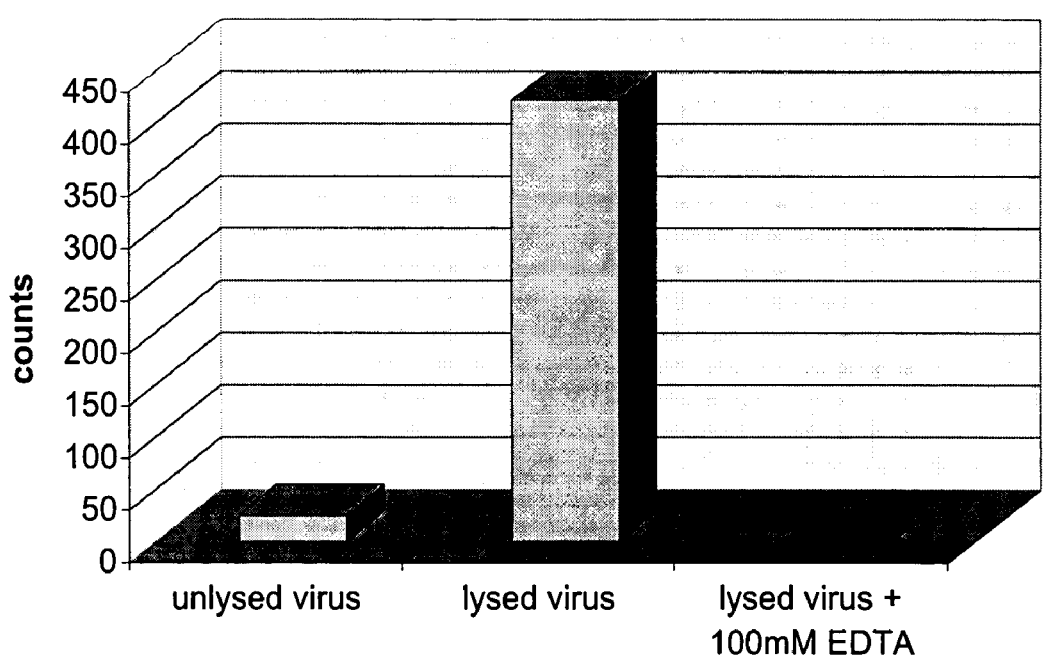
FIG. 3 shows activity of the Murine leukemia virus-Luciferase (Fr-luc) virus particles (10 ul of culture supernatant) in luciferase assay buffer. Activity increased when particles were lysed in 0.1% NP-40 detergent and was abolished by the addition of EDTA as indicated. This indicated that the luciferase was incorporated into the virus particles and likely enveloped by the viral lipid membrane. Lysis released the luciferase enzyme. EDTA chelates the $Mg^{2+}$ co-factor and inhibits the luciferase reaction.
Figure 4:
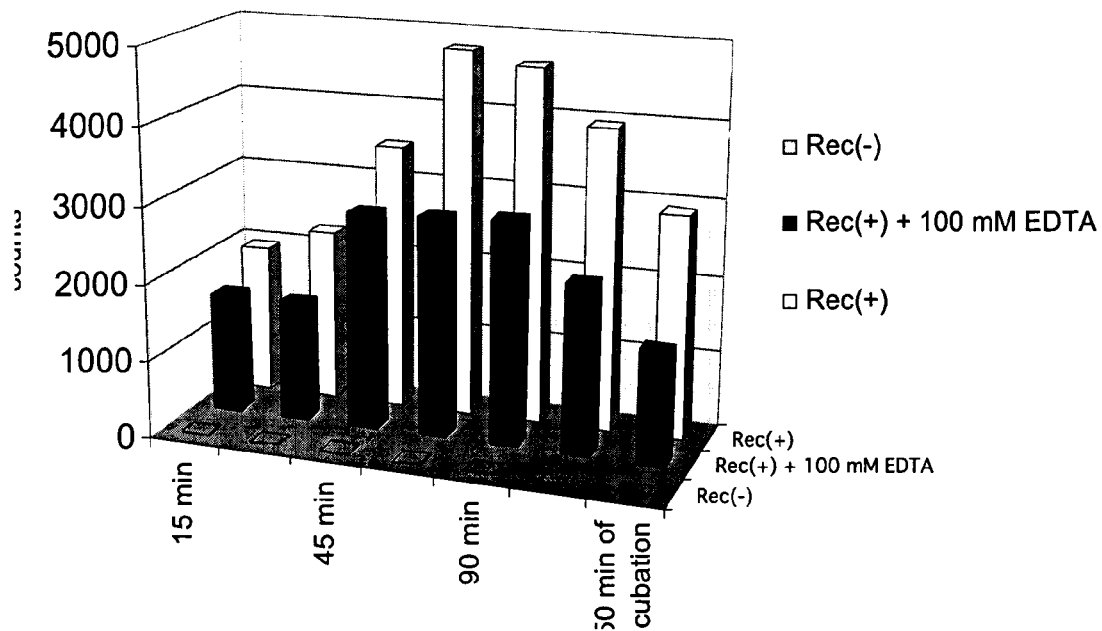
FIG. 4 shows time course of attachment and entry of the Fr-luc virus particles to cells lacking (Rec−) or bearing receptor (Rec+).
Figure 5:
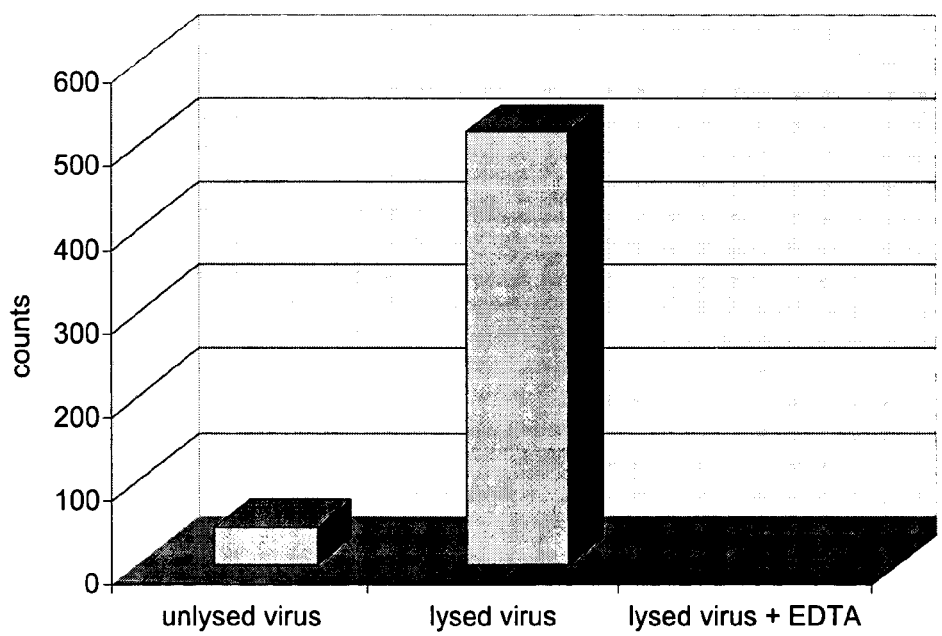
FIG. 5 shows mosaic viruses made between the VSV-G envelope and the Fr-Luc proteins by making a mixed transfection of producer cells. These particles behaved identically to the Fr-luc viruses in FIG. 1.
Figure 6:
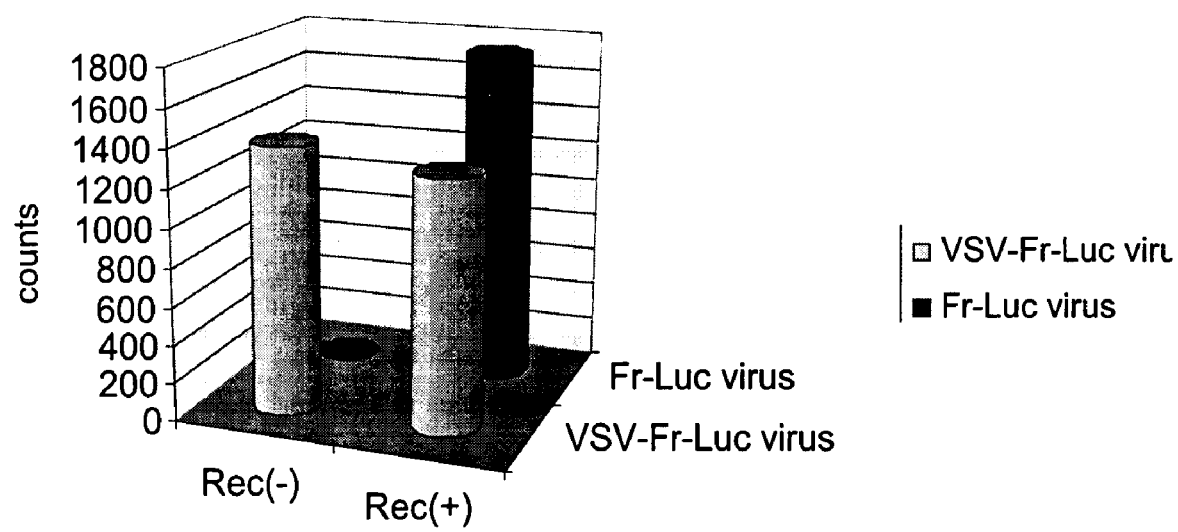
FIG. 6 shows that when applied to cells, the VSV-G+Fr-luc particles adopted the entry profile of Vesicular Stomatitis-Virus. Particles were applied to cells lacking or bearing the Fr-luc receptor but both sharing the Vesicular Stomatitis Virus receptor. Both cell types gave equal signals for the Vesicular Stomatitis Virus mosaic viruses but only that bearing the Fr-luc receptor gave a similar signal. This data demonstrates the versatility of the system in being adapted to measure cell/receptor binding and entry for other virus types without extensive modification.

In another embodiment, viruses would be assembled as described above, except wild type envelope proteins are replaced with foreign envelope proteins of interest. The envelope-luciferase construct simply provides a mechanism to deliver the luciferase into the virus particles and should be generic. When assayed on human cells or any cells other than mouse or rat, these mosaic viruses (FIG. 2) would have specificity dictated by the foreign envelope proteins. If needed the envelope-luciferase construct can be modified such that it no longer interacts with the receptors found on rat/mouse cells. This will then permit use of mouse or rat cells as well. Vesicular Stomatitis Virus-MLV mosaic viruses were made to test this approach. It was determined that the assay performed well, and it was possible to measure entry into human cells with signals similar to those described above.

In another embodiment, there is provided a method of evaluating amino acid substitutions on virus binding and entry. The method steps include making a mutant containing an amino acid substitution in a viral envelope protein; attaching an enzyme to the C-terminal end of a viral envelope protein, thereby creating a envelope-enzyme fusion protein; generating virus particles comprising the fusion protein and the mutant viral envelope protein; infecting target cells with the virus particles and measuring enzyme activities in the lysed and intact infected cells, thereby enabling evaluation of amino acid substitutions on virus binding and entry. All other aspects regarding the enzyme, viral protein-enzyme fusion protein, and ability of the assay to work in 96-well plate format are as described earlier.

In yet another embodiment, there is provided a method for determining whether the viral entry mechanism is pH-dependent. Assays for binding and entry are carried out as described above in the presence or absence of inhibitors of endosomal acidification, wherein decreased enzyme activities in the presence of endosomal inhibitors indicates the virus has a pH-dependent mode of entry. All other aspects regarding the enzyme, viral protein-enzyme fusion protein, wild type envelope protein and ability of the assay to work in 96-well plate format are as described earlier.

In yet another embodiment, there is provided a method of receptor-dependent targeted delivery of a therapeutic protein, comprising the steps of attaching a therapeutic protein to the C-terminal end of a viral envelope protein, thereby creating a fusion protein; and generating virus particles comprising the fusion protein and wild type viral envelope protein. Targeted delivery of therapeutic protein would be mediated by binding of the wild type envelope protein. Preferably the therapeutic protein is a toxin, a chemotherapeutic agent, an immune stimulant, cytotoxic agent or a radioisotope. All other aspects regarding the enzyme, viral protein-enzyme fusion protein, wild type envelope protein are as described earlier.

Additionally, the present invention is also directed to a pharmaceutical composition comprising therapeutic protein-containing virus as described above. All other aspects regarding the enzyme, viral protein-enzyme fusion protein, wild type envelope protein, the type and size of therapeutic protein are as described earlier. Preferably, the pharmaceutical composition comprises the novel active composition of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" $15^{th}$ Edition, pages 1035-1038 and 1570-1580). Some variation in dosage will necessarily occur depending on the condition of the subject being treated. The person responsible for administration will, in any event, determine the appropriate dose for the individual subject.

In another embodiment, there is provided a method for screening neutralizing antibodies in sera. Assays for virus binding and entry are carried out as described earlier, where decreased enzyme activities in the presence of the sera indicates that the sera has neutralizing antibodies. All other aspects regarding the enzyme, viral protein-enzyme fusion protein, wild type envelope protein and ability of the assay to work in 96-well plate format are as described earlier.

In yet another embodiment, there is provided a diagnostic kit for screening neutralizing antibodies in sera, where the kit comprises (a) enzyme-containing virus pseudotypes and (b) substrate for the enzyme. All other aspects regarding the enzyme, viral protein-enzyme fusion protein, wild type envelope protein are as described earlier.

In still yet another embodiment, there is provided a method of screening for compounds that inhibit virus binding and entry into target cells. The assays for virus binding and entry are carried out as described above in the presence or absence of the test compound, where decreased enzyme activities in the presence of the test compound indicates that the compound inhibits virus binding and entry into target cells. All other aspects regarding the enzyme, viral protein-enzyme fusion protein, wild type envelope protein and ability of the assay to work in 96-well plate format are as described.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, the term "PCR" refers to the polymerase chain reaction that is the subject of U.S. Pat. Nos. 4,683,195 and 4,683,202 to Mullis, as well as other improvements now known in the art.

As used herein, "restriction endonucleases" and "restriction enzymes" refer to enzymes, each of which cut double-stranded DNA at or near a specific nucleotide.

The term "oligonucleotide", as used herein, is defined as a molecule comprised of two or more ribonucleotides, preferably more than three. Its exact size will depend on many factors, which, in turn, depend upon the ultimate function and use of the oligonucleotide. The term "primer" used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may either be single-stranded or double-stranded and must be sufficiently long to prime the synthesis of the desired extension product in the presence of inducing agent. The exact length of the primer will depend upon many factors, including temperature, sequence and/or homology of primer and the method used. For example, in diagnostic applications, the oligonucleotide primer typically contains 15-25 or more nucleotides, depending upon the complexity of the target sequence, although it may contain fewer nucleotides.

The primers used herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary bases with the sequence to hybridize therewith and form the template for synthesis of the extension product.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Virus Entry Assay Protocols

The envelope-luciferase fusion vector was made by modifying the 3' end of the Friend 57 Murine Leukemia Virus envelope protein to replace the native stop codon with an EcoRV restriction endonuclease site. This was achieved using PCR. Primers used: 5' CCATCGATTAGT-TCAATTTGTTAAAGACAG 3' (SEQ ID NO.1) and 5' GATCGAATTCTGGCTCGTATTCTAGTGGTTTTAGC 3' (SEQ ID NO.2). The firefly luciferase gene was modified to gain an EcoRV restriction endonuclease site at its 5' end. A short linking peptide (Serine-Glycine) was also added in the same reaction. The primers used: 5' GATCGAATTCGAA-GACGCCAAAAACATAAAGAAAG 3' (SEQ ID NO.3) and 5' GATGCGGCCGCTTACACGGCGATCTTTC-CGCCCTT 3' (SEQ ID NO.4). The latter primer also gave two tandem stop codons followed by a NotI restriction endonuclease site at the 3' end of the gene. The recombinant MLV envelope gene was then cloned into a standard expression vector (pCDNA3) using a native HindIII site at its 5' end and the artificial EcoRV site. The modified luciferase gene was then added using sites EcoRV and NotI. The construct was sequenced and had the predicted nucleotide sequence.

The construct was tested by producing MLV pseudotyped viruses bearing the envelope-luciferase fusion protein. To do this cells were simultaneously transfected with plasmids encoding 1) the envelope-luciferase fusion protein, 2) the MLV polymerase, capsid and matrix proteins (gag-pol gene) and 3) a packageable marker gene such as b-galactosoidase or jellyfish green fluorescent protein (permits determination of virus titer by conventional gene expression methods). Transfection was by standard calcium phosphate mediated transfection methods. After two days the supernatant was collected and filtered through a 0.45 mm cellulose acetate filter and either used immediately or frozen at −80° C. To perform an entry assay, fresh cells ($10^4$-$10^5$) were incubated with 0.2-1.0 ml of virus containing culture supernatant for times up to 2 hours. Cells were then collected by 1 min centrifugation at 1000×g and the supernatant was aspirated off.

It has been previously shown that intact cells can be efficiently perfused with luciferin (the luciferase substrate). This provides a simple and rapid way to measure if virus has fused to the cell membrane by measuring release of the encapsidated luciferase enzyme into the luciferin and ATP (substrates of luciferase) containing cytoplasm of the cell. Therefore, isotonic luciferase buffer (modified from Promega by addition of sodium acetate to 50 mM) was added.

To ascertain the amount of virus that had penetrated the cell versus that bound on the surface, cells were either incubated intact (shows how much virus entered the cell by fusion with the cell membrane) in this buffer or lysed (total=entered+bound on surface) in 0.1% NP-40 detergent. Measurements were made using a standard luminometer after 5 minutes but could be performed sooner without much change in the signal.

As the entry assay relies on the encapsidation of the marker enzyme (luciferase) within the luciferin impermeable viral membrane it was necessary to optimize conditions to achieve this. The amount of plasmid encoding the native envelope protein was adjusted from 0 to 5 mg and sufficient envelope-luciferase encoding plasmid was added to give a total of 5 mg in the transfection mixture. It was found that 5 times more native envelope protein was optimal for virus particle production, maximal luciferase activity in detergent lysed virus and minimal activity in unlysed particles. This indicated that under these conditions the luciferase protein is efficiently encapsidated in intact virions. Reducing the amount of native envelope encoding plasmid resulted in particles that gave lower virus titer. They also gave luciferase activity without lysis. This indicated that the particles were defective, with breaches in the viral envelope membrane and were not suitable for use in this assay.

To perform the assay in 96 well format, $10^4$ cells were seeded into each well and 0.2 ml of virus containing culture supernatant was incubated with the cells for 1 hour. After this time the supernatant was removed and luciferase buffer (as above) was added with or without detergent. The plates were then analyzed in a standard luminescent plate reader.

Assays were also performed without removal of the culture supernatant by addition of the luciferase buffer directly to the mixture. In this case the signal was approximately 80% that obtained when the culture medium was completely replaced.

EXAMPLE 2

Construction of Envelope-Luciferase 1 (env-luc1) and Envelope-Luciferase 2 (env-luc2) Constructs It is known that the envelope protein of the murine leukemia virus (MLV) is made as a single polypeptide that is cleaved in the endoplasmic reticulum into two subunits, SU (70 kDa) and TM (15 kDa). TM that anchors the complex to the cell and eventually to virus membranes is cleaved by a viral protease to release a C-terminal peptide, p2e immediately before or just after budding from cell. This has been shown to be important for infection competency of the virus. Therefore, fusion of proteins to the C-terminus of T M would provide a novel method of delivering recombinant protein to the viral lumen, between the membrane and matrix shell of the viral core. The cleavage of the protein by viral protease after budding would also release the luciferase permitting it to diffuse into the cell cytoplasm after membrane fusion.

To demonstrate this, two constructs, env-luc1 and env-luc2 differing in the length of the spacer peptide that fused the Friends57 MLV envelope to the N-terminus of the luciferase gene (FIG. 7A) were made. The env-luc fusion vector was made by modifying the 3' end of the Friend57 murine leukemia virus (MLV) envelope gene to replace native stop codon with an EcoRI restriction endonuclease site. This was achieved using PCR. Primers used were SEQ ID NO.1 and SEQ ID NO.2. The firefly luciferase gene was modified to gain an EcoRI restriction endonuclease site at its 5' end. A short linking peptide (Glu-phe) and (Glu-Phe-Gly-Ser, SEQ ID NO.5) for env-luc1 and env-luc2 respectively was added in the same reaction through the EcoRI site. The primers used were SEQ ID NO.3 and SEQ ID NO.4. The later primer also gave two tandem stop codons, followed by a NotI restriction endonuclease site at the 3' end of the gene. The recombinant MLV envelope gene was then cloned into pCDNA3 (Invitrogen) using a native HindIII site at its 5' end and the artificial EcoRI site. The modified luciferase gene was then added using EcoRI and NotI sites. The constructs were sequenced and had the predicted nucleotide sequence.

The MLV viruses were made with env-luc1 and env-luc2 constructs and pψ-EGFP plasmid substituted pFB-luciferase vector, thereby permitting direct determination of virus titer by infecting cells and counting colonies expressing EGFP.

In general, the production of pseudotyped MLV and viruses containing envelope-luciferase fusion protein can be explained briefly as follows: 293 HEK cells grown to 80% confluence were transfected by calcium phosphate method. Plasmids used were (5 µg each): (1) pGAG-POL, encoding the MLV gag and polymerase; (2) pEnv (Friend57 envelope protein in pcDNA3) or pVSV-G (G protein of vesicular stomatitis virus); and (3) pψ β-gal or pψ EGFP, encoding β-galactosidase or enhanced green fluorescent protein respectively under control of MLVLTR and packaging sequence. To make virus containing the env-luc1 fusion protein, 1 µg of this construct was added to the mixture unless stated otherwise. After overnight incubation, the medium was replaced with fresh medium and incubated for a total of 36 hours. The supernatants were then collected and filtered through a 0.45 µm cellulose acetate filter. The filtrate was then used either directly or the virus is pelleted by 1 h centrifugation at 16,000×g and the pellet used. In some experiments, virus was collected by pelleting through cushion of 20% (w/v) sucrose, 10 mM Tris-HCl, pH 7.4.

Luciferase was present in the supernatant for both constructs. Most of this activity was also pelleted by centrifugation and penetrated a 20% sucrose cushion at 20,000×g, a characteristic of intact MLV particles. The pelleted material was also associated with infectious virus and gave the titers of $3\times10^3$ and $4\times10^4$ cfu/ml for env-luc1 and env-luc2, respectively. In later experiments, sucrose gradients (5-60%) were also used to purify the virus. Greater than 90% of the luciferase activity comigrated with the infectious virus peak.

Figure 7B:
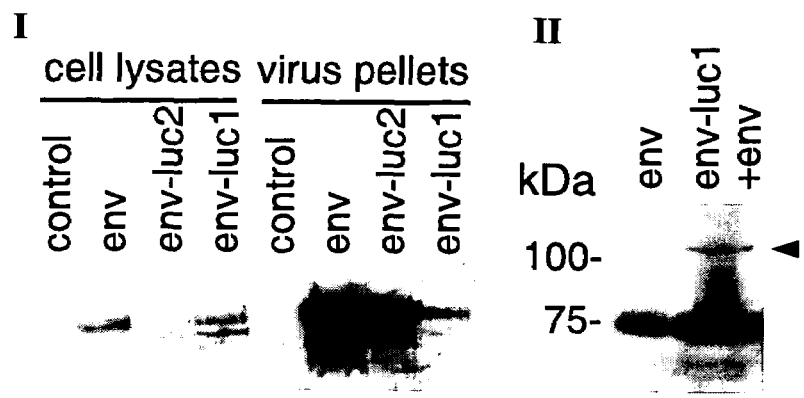
Figure 7C:
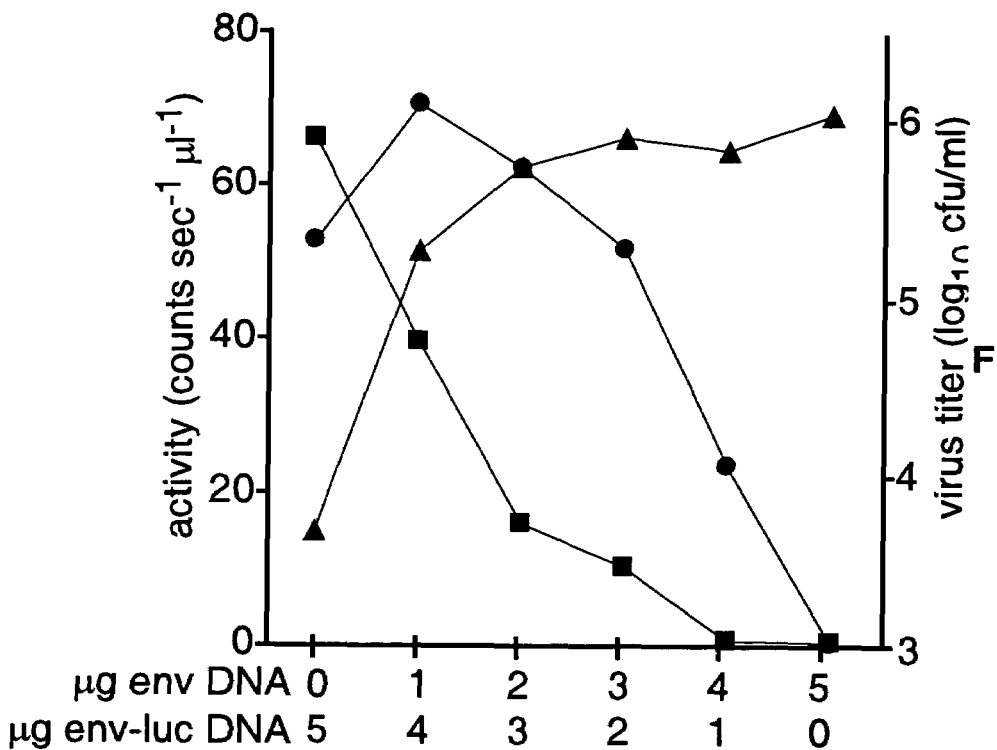

Western blots probed with anti-SU showed differences in the levels of production of each construct in the cells and incorporation in particles (FIG. 7B (I)). Each was processed rapidly to the native SU band. The env-luc1 protein was produced at similar levels to wild type envelope protein, while lower amounts of env-luc2 were detected. However, env-luc2 was incorporated more efficiently in particles than env-luc1. By increasing the amount of plasmid encoding wild type envelope protein in the transfection mixture, an uncleaved precursor for env-luc1 was observed in cell lysates migrating above 100 kDa (FIG. 7B (II), right panel), this band was absent in the pelleted material. This indicated that the env-luc protein was processed correctly by cellular proteases into SU and TM. Although attempts to detect luciferase-TM product on Western blots were unsuccessful due to lack of a sensitive anti-luciferase antibodies (data not shown), the fact that luciferase was present in the infection mixture indicated that enzyme had been successfully incorporated.

To measure entry, the luciferase would have to be encapsidated in intact virions impermeable to the luciferase substrates. The luciferase activity was measured in the presence or absence of 1% NP-40, which permeabilize MLV that are normally impermeable to small solutes such as dNTPs. It was observed that virus made with env-luc1 gave a 3-fold higher luciferase activity than the virus made with env-luc2. However, it was observed that addition of NP-40 increased the signal for both env-luc1 and env-luc2. The ratio of luciferase activity for lysed versus unlysed virus for env-luc1 was 15 and for env-luc2 was 1. This indicated that although both the constructs successfully targeted luciferase into the virus, incorporation of env-luc2 was more disruptive, resulting in a greater number of membrane breaches compared to most virus made with env-luc1, which were intact (Table 1). This also indicated that the particles have a finite capacity for luciferase and that env-luc1 limits this by being poorly incorporated.

In order to optimize the virus production, the titer of virus made with env-luc1 was raised ($10^3$ cfu/ml compared to $10^6$ cfu/ml for wild type virus) by addition of wild type envelope encoding plasmid in the transfection mixture. The ratio of env-luc1 to wild type envelope encoding plasmid was adjusted and the lysed:unlysed luciferase signal ratio and virus titer were measured by marker gene expression (FIG.

7C). It was observed that a ratio of 4:1 env-luc1 to wild type envelope plasmid, gave a virus of low titer and high lysed:unlysed signal ratio compared to ratio of 1:4, which improved the virus titer to $1\times10^6$ cfu/ml, similar to wild type envelope plasmid alone and a lysed:unlysed signal ratio of 10:1. Over a series of six separate experiments, the average ratio was 11.2+/−3.7. Thus, together these data indicated that these virus particles should act as a molecular beacon, with signal being produced after the luciferase is released by fusion of cell and virus membrane and a signal to noise ratio of at least 10-fold.

In order to determine if these particles would produce a receptor-dependent entry signal, these particles were incubated with 293 cells bearing receptor (293-CAT) or lacking receptor (293). 293 cells are not permissive for ecotropic MLV infection until they are made to express mCAT-1, the ecotropic MLV receptor and hence, these served as a negative control. A clone of 293 cells expressing recombinant mCAT-1 with a c-terminal HA-tag, termed 293-CAT was used as a target.

In general, the entry assay was performed by incubating cells (typically $10^5$/sample) for 1 h with env-luc1 containing virus at an MOI of 0.1-0.5. Excess virus was washed free of cells by pelleting by centrifugation at 200×g for 5 min and resuspending in DMEM. The cells were pelleted again and resuspended in 0.1 ml of luciferase assay buffer (Promega). Luciferase activity was measured after 1 min in a Turner Designs TD 20/20 luminometer and expressed as counts/sec. The assay was also performed in a 96-well plate using $10^4$ cells per well. While the signal was reduced proportionally, it remained at least 10-fold above the background of the detector (Perkin-Elmer plate reader).

Figure 8:
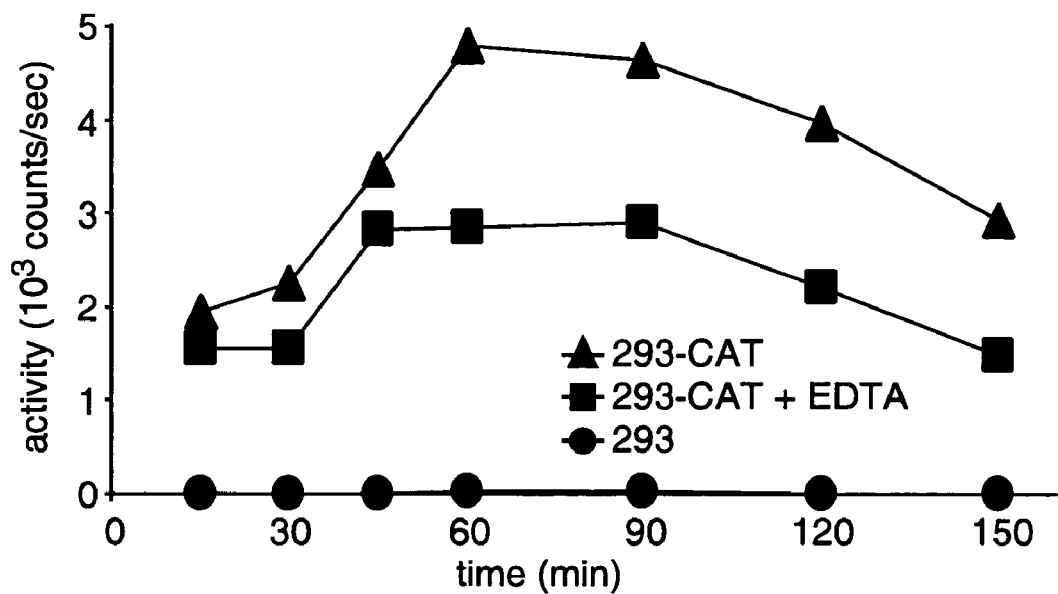
FIG. 8 shows luciferase activity of virus mixture incubated over time with 293 cells bearing receptor (293-CAT, triangles) and not when incubated with 293 cells lacking receptors (293, circles) in intact cells. It also shows the amount of luciferase that was exposed on the cell surface by adding EDTA (100 mM, squares) immediately before the addition of the luciferase substrates.

In this case, cells were incubated in the presence of 0.5 ml of virus containing culture medium for times up to 2 h at 37° C. with gentle mixing. Cells were then pelleted, washed free of unbound virus and assayed for luciferase activity by incubating the cells directly in luciferase buffer. Signals were detected on cells bearing virus receptor. The signals peaked 1 minute after addition of the assay buffer, which was consistent with rapid uptake and equilibration of luciferin into the cells (FIG. 8, triangles). Similar kinetics was observed with cells transfected with a luciferase-encoding plasmid (pFB-luc, data not shown). Cells expressing the receptor gave a signal that peaked after 1-1.5 h at 5000 counts/sec (FIG. 8, triangles). No activity above the background signal of the luminometer (approx. 10 counts/sec) was observed for 293 cells. In other experiments, it was observed that the magnitude of the signal changed in direct proportion to the number of receptor-bearing cells ($10^4$-$10^7$) or amount of virus used (MOI of 0.01-10). These observations demonstrated that particles containing luciferase were successfully targeted to receptor bearing cells, which produced a signal that was consistent with receptor-dependent exposure of the enzyme.

In order to determine the portion of the signal from virus having entered the cell from that of particles that had broken open on the cell surface, suspension or residual defective particles, 100 mM EDTA (isotonic), pH 7.4 was added to the sample. Since luciferase requires MgATP to function, this treatment effectively inhibits activity by sequestering the $Mg^{2+}$ present in the supernatent. It was observed that the signal dropped on average, by 30% with the remainder being resistant (FIG. 8, squares). In other experiments, EDTA inhibited the activity to 10-20%. These observations were consistent with the virus-associated luciferase being taken into an EDTA-inaccessible compartment by either receptor-dependent endocytosis or fusion of the virus membrane with cell membranes. The EDTA-sensitive portion may be due to the residual permeable, defective particles bound to cells or virus in early stages of entry that may be more easily disrupted.

TABLE 1

Encapsidation of Luciferase Into Virus Particles

| Plasmids Transfected | | | | | | Luciferase Activity (counts/sec/10 µl) | | | |
|---|---|---|---|---|---|---|---|---|---|
| PFB-Ψluc | PΨEGFP | pGag-pol | pEnv | pEnv-luc1 | pEnv-luc2 | Cell Lysate | Supernatant | Pellet | Ratio |
| − | + | + | + | − | − | 0 | 10 | 8 | n.d. |
| + | − | + | + | − | − | 574,000 | 1,101 | 22 | n.d. |
| − | + | + | − | + | − | 2,212,000 | 556 | 975 | 15 |
| − | + | + | − | − | + | 2,022,000 | 350 | 243 | 1 |
| − | + | + | + | + | − | n.d. | 2,145 | 2,891 | 11 |

293 cells transfected with the plasmids as indicated and the luciferase activity in the supernatants was tested after harvesting (36 h after transfection) and filtering (0.45 µm). Part of the supernatant (0.25 ml) was overlayed on a 0.5 ml 20% (w/v) sucrose cushion and pelleted material was collected after 1 h at 16,000×g. Cells and pellets were lysed by resuspension in 1.0 ml or 01 ml of 1% NP-40, respectively. 10 µl was then used to determine the luciferase activity. Ratio equals to luciferase activity in lysed to unlysed cells. N.d.=not determined.

EXAMPLE 3

Figures 9A, 9B:
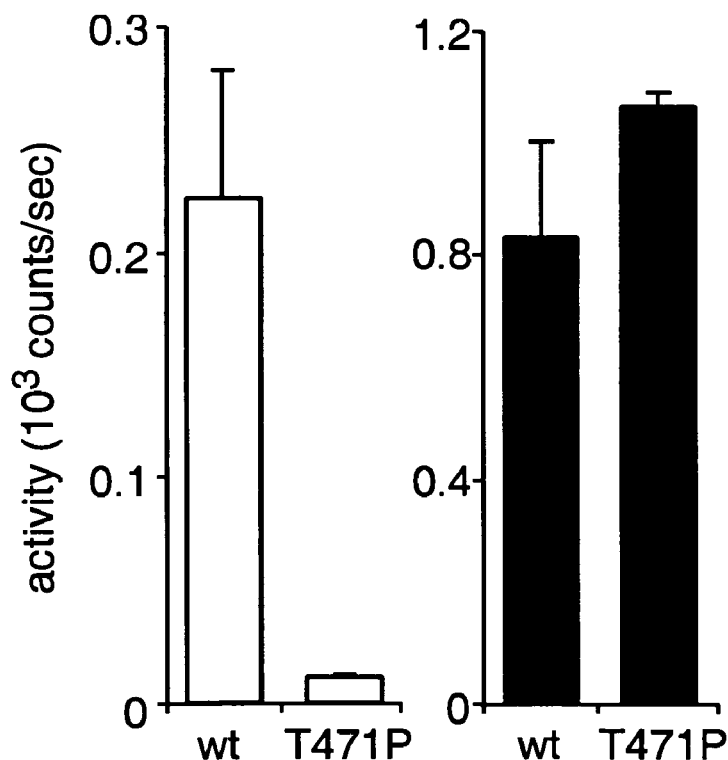
FIG. 9A-9B shows the measurement of luciferase activity for analysis of fusion peptide point mutation, T471P using the entry assay. A single amino acid substitution, T471P was made in the Friend MLV envelope protein and in the env-luc1 construct. Virus was produced, lysed in 1% NP40 and matched to luciferase activity of virus-bearing wild-type envelope protein and env-luc1. This was applied to cells and the luciferase activity was measured after 1 hour on intact cells (FIG. 9A, left panel) or in the presence of 1% NP40 (FIG. 9B, right panel).

Introduction of a Single Amino Acid Substitution in Friend MLV Envelope Protein and in the Env-Luc1 Construct To further confirm that the signal measured was due to penetration of the virus-associated luciferase into cells through virus mediated membrane fusion, a point mutation, T471P was introduced in the envelope protein. This change was previously characterized and shown to bind cells but not infect them. The fusion peptide mutant was made by PCR mediated site directed mutagenesis. The sense strand oligonucleotide for the T471P mutation was 5' CGCCGCGG-GAGTTAGGGCCCGGAACTACCGCC 3' (SEQ ID NO.6), which added an ApaI endonuclease site (underlined). The fragment of DNA encoding the changes was cloned into native KpnI and ClaI sites in the Friend57 ecotropic envelope gene and into env-luc1 construct. Base changes were confirmed by restriction enzyme cleavage using ApaI and sequencing. The mutation was placed in both the Friend MLV envelope protein and the env-luc1 construct. Virus was produced and cells were challenged. The supernatant containing virus with the T471P mutation gave a similar luciferase activity to that of the wild type of 40 counts/sec/μl and a typical lysed:unlysed ratio of at least 5. After 1 hour of incubation, the T471P mutant gave a signal that was close to the background signal of the luminometer and 20-fold lower than that for wild type virus (FIG. 9A, left panel). Addition of 1% NP-40 detergent to expose the encapsidated luciferase and permit determination of total cell-associated virus, gave similar activities for both wild type and the T471P mutant (FIG. 9B, right panel). In a separate experiment, little activity was present in 293 cell lysates. This indicated that the T471P mutant virus had bound to cells normally but had not exposed the encapsidated luciferase. Together these data strongly support the conclusion that the assay is measuring receptor-mediated fusion of virus to cells and delivery of the luciferase enzyme in cell cytoplasm.

EXAMPLE 4

Production of MLV Pseudotype Bearing the Envelope Protein of Vesicular Stomatitis Virus To demonstrate that the luciferase could measure inhibition of entry for a pH-dependent virus, an MLV pseudotype bearing the envelope protein of vesicular stomatitis virus (VSV-G) together with env-luc1 was constructed. The VSV pseudotypes of MLV have been previously reported and enter cells through a VSV-G dependent mechanism possibly by clathrin-mediated endocytosis. VSV have also been shown to a have a pH-dependent fusion mechanism in vitro. Since the env-luc1 protein would not participate in entry if assays were performed on 293 cells lacking the ecotropic receptor as shown by data in FIG. 8, a VSV-G/env-luc1 chimeric virus was made by substituting the Friend envelope expression plasmid with that of VSV-G as stated earlier. The VSV-G/env-luc chimeric virus was collected and gave a lysed:unlysed ratio of 8.7+/−2.2, which was slightly lower than that for the original Friend envelope containing virus but still demonstrating that most of the particles encapsidated luciferase. The overall activity of the lysed particles was one-half of the Friend virus, being 10 counts/sec/μl of culture supernatent.

The activity of three inhibitors of endosomal acidification on the VSV-G and Friend MLV luciferase-containing viruses was then tested. In general, the cells were treated with lysosomotropic agents chloroquine, bafilomycin A1 and ammonium chloride. Ammonium chloride and chloroquine were dissolved directly in DMEM and incubated with cells for 1 h before and during incubation with virus. Bafilomycin A1 was first dissolved in DMSO as a 50 μM stock and diluted in DMEM before use. Each of the three drugs were compared by measuring the effect on the infection efficiency, as measured by staining in a conventional reporter gene expression assay, after 2 days or in the luciferase entry assay after 1 hour incubation (FIG. 10). In this experiment, the number of cells ($10^6$) and the virus used per sample were increased by 10-fold. This gave a proportional increase in signal and sensitivity.

The β-galactosidase infection assay that measured the reporter enzyme expression after 36 hours showed that infection of VSV-G pseudotype was more sensitive to each drug, with bafilomycin being the most potent, reducing infection by 100-fold at 40 nM (FIG. 10A, solid bars). The luciferase assay, by comparison was more sensitive for the VSV-G pseudotypes. It was observed that 20 mM and 40 nM of ammonium chloride and bafilomycin respectively, decreased the signal by 1000 to 10,000-fold (FIG. 10B, right panel, solid bars). Chloroquine, which was not as effective, inhibited the infection and the entry signal by only 20 and 7-fold respectively. When the Friend pseudotype was used, the infection was inhibited weakly by all of the drugs up to 3-fold which, represents a relatively small decrease in virus titer from $10^6$ to $3 \times 10^5$ cfu/ml. Similarly the luciferase activity for this virus was decreased by no more than 2-fold (FIG. 10B, open bars). In comparison to VSV-G pseudotype, this change is small and reflects slight cytotoxic effects of each drug on the cells.

To check that the drugs did not alter the permeability of cells to luciferin and access to ATP, cells were infected with a luciferase expressing retrovirus made using the plasmid, pFB-ψluc (Stratagene) and luciferase activity was measured two days later. At the concentrations of inhibitor used, little change in the signal was observed after the cells were incubated in luciferase buffer.

In addition the cells were incubated with luciferase containing Friend and VSV-G pseudotyped virus and the drug was then added after 1 hour and luciferase activity measured. When assayed for activity, the cells showed similar small changes in signal compared to cells pre-incubated with drug (data not shown). These data taken together strongly indicated that the assay measured the entry of virus and confirmed that the inhibitors of endosomal acidification did not significantly affect the entry of ecotropic MLV.

Figure 11:
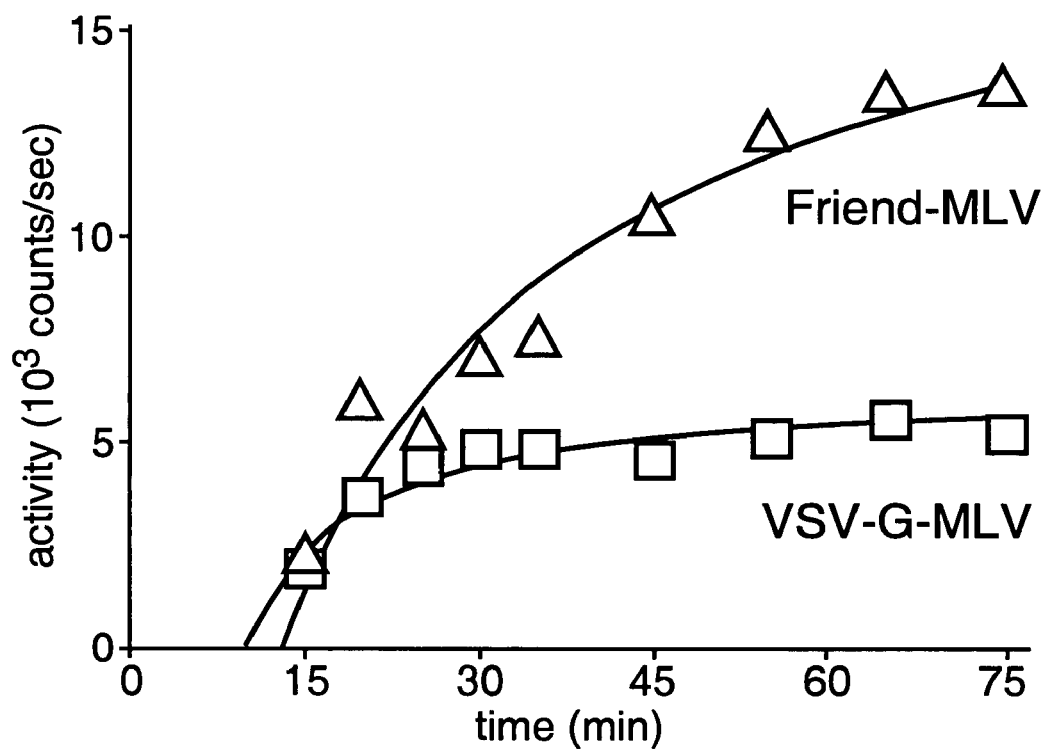
FIG. 11 shows pulse chase analysis of entry kinetics using the luciferase assay. Cells ($2 \times 10^6$) were incubated with luciferase containing Friend-MLV (triangles) or VSV-G MLV (squares) pseudotyped virus at an MOI of 0.5 for 5 minutes at 37° C. Samples were then collected at the times indicated (calculated from the time of virus addition) and activity was measured as described previously. Curves (rectangular hyperbola) were fitted to data by non-linear regression analysis using GraphPad Prism version 4.00 for Windows, (GraphPad Software, San Diego, Calif., USA).

Since the kinetics of entry for MLV was poorly understood, a pulse-labeling experiment was performed, using the luciferase assay to measure the virus entry of Friend MLV and VSV-G pseudotypes. The particles were incubated with 293 or 293-CAT cells for 5 minutes and unbound virus were removed by rapid washing. Cells were then incubated at 37° C. with gentle agitation and the luciferase activity was measured at different time points for up to 75 minutes (FIG. 11). For both the pseudotypes, the earliest time point at which the luciferase activity was detectable was 10 minutes after the excess virus had been removed by washing. For the Friend MLV, this signal grew steadily and began to plateau at 75 minutes (FIG. 11). A non-linear regression analysis showed that half of the particles had fused with cells by 40+/−1.3 minutes post binding ($R^2$=0.94). For the VSV-G MLV pseudotype, it was observed that the kinetics was more rapid, reaching a plateau at 30 minutes (FIG. 11). A similar linear regression analysis showed that the half of signal was reached by 18+/−1.2 minutes ($R^2$=0.87). The signal obtained from the VSV MLV was approximately 3-fold lower than that for Friend MLV.

To test if this difference was due to lower amounts of VSV MLV virus being bound to cells and to ensure that similar amounts of virus had remained bound to cells during the chase phase of the experiment, $^{35}$S-methionine labeled, density gradient purified virus was included in the assay. The $^{35}$S-methionine labeled virus were produced as follows. One day after transfection with plasmids, cells were washed twice in DMEM, and then incubated overnight in methionine-free DMEM, containing 0.25 mCi of cell labeling grade 35s-methionine (Amersham). Virus containing supernatants were collected, filtered and particles were pelleted through a 20% sucrose cushion by centrifugation at 20,000×g for 3 hours. The pellet was collected in PBS and used. To ensure that radioactivity was associated with the virus particles, some of the supernatent was applied to a Sepharose CL-4B column (Sigma) and the amount eluting with the void volume and retained volumes was measured by scintillation counting. 80-90% radioactivity was observed in the void for VSV and Friend MLV, indicating that it was most likely associated with the virus particles and was not free methionine. Cells were then incubated for 5 minutes with virus and rapidly washed three times, by gentle pelleting at 200×g for 3 min and resuspension in DMEM. They were then incubated at 37° C. with gentle agitation and used for measurements at the times given.

Over the entire time course, it was observed that the cell associated virus remained relatively constant with an average of 4.3+/−0.4% of the input VSV-G containing particles being bound to cells, corresponding to a final MOI of 0.002 (titer of virus on 293-CAT cells was $1.3×10^6$ cfu/ml). For the Friend MLV 10.4+/−1% of the input virus was cell associated, corresponding to MOI of 0.006 (titer was $1.5×10^6$ cfu/ml). These results indicated that the observed difference in the VSV-MLV and Friend MLV plateaus was due to the amount of virus that had bound during the 5 min pre-incubation and that a similar proportion of each was able to yield a signal. In other experiments, with extended time courses, it was observed that by 2.5 hours, the signal had dropped to 60% of the peak at 75 min, similar to FIG. 8. This indicated that the signal was labile with a half-life of >2.5 h. However, this slow decay should have little effect on the above analysis.

EXAMPLE 5

Pseudotyped Viruses Comprising Luciferase-HIV Nef Fusion Protein

This example describes pseudotyped viruses comprising luciferase-HIV Nef fusion protein. The HIV Nef protein normally associates with the inner side of HIV virus membrane. Upon binding and entry into target cell, the Nef-Luciferase fusion protein becomes exposed and the activity of the luciferase can be measured immediately. Thus, the activity of luciferase following exposure of cells to pseudotyped particles is a direct measure of virus fusion and entry.

The following data show that luciferase signal substantially decreases if virus entry is inhibited, e.g. by neutralizing antibodies or specific entry inhibitors (such as ENFURVITIDE in the case of HIV). Thus, this viral entry assay provide a means to identify/discover novel entry inhibitors, and directly determine pharmacokinetics of existing compounds. Currently both of these objectives are not readily achieved by prior art techniques, particularly for viruses such as HIV and high containment pathogens. In addition, this entry assay can also be used as a serodiagnostic assay and can potentially replace more time-consuming and cumbersome assays, such as plaque reduction neutralization test. An important feature of this system is that since the entry of pseudotyped particles is dependent on envelope protein incorporated into the pseudotyped virus, this assay could potentially be used for any enveloped virus that can be pseudotyped and provides a standardized, diagnostic platform technology.

The HIV-Nef-luciferase fusion protein (nef-luc) was made by PCR-based amplification of the Nef encoding region from plasmid p96ZM651nef-opt (NIH AIDS reference reagent program). The oligonucleotide primers used were 5' AT GGATCCATGGGCGGCAAGTGGAGCAAG 3' (SEQ ID NO.7) and 5' TAGAATTCGCAGTCCTTGTAG TACTCGGG 3' (SEQ ID NO.8). The 5' oligonucleotide placed a BamHI site (underlined) and an initiation codon (italics) at the 5' end of the Nef gene. The 3' oligonucleotide placed an EcoRI site (underlined) suitable for an in-frame fusion with the previously modified luciferase gene from Example 2. The Nef-encoding fragment was then inserted in-frame with that encoding the luciferase enzyme in the plasmid vector pCDNA3.

Figure 12:
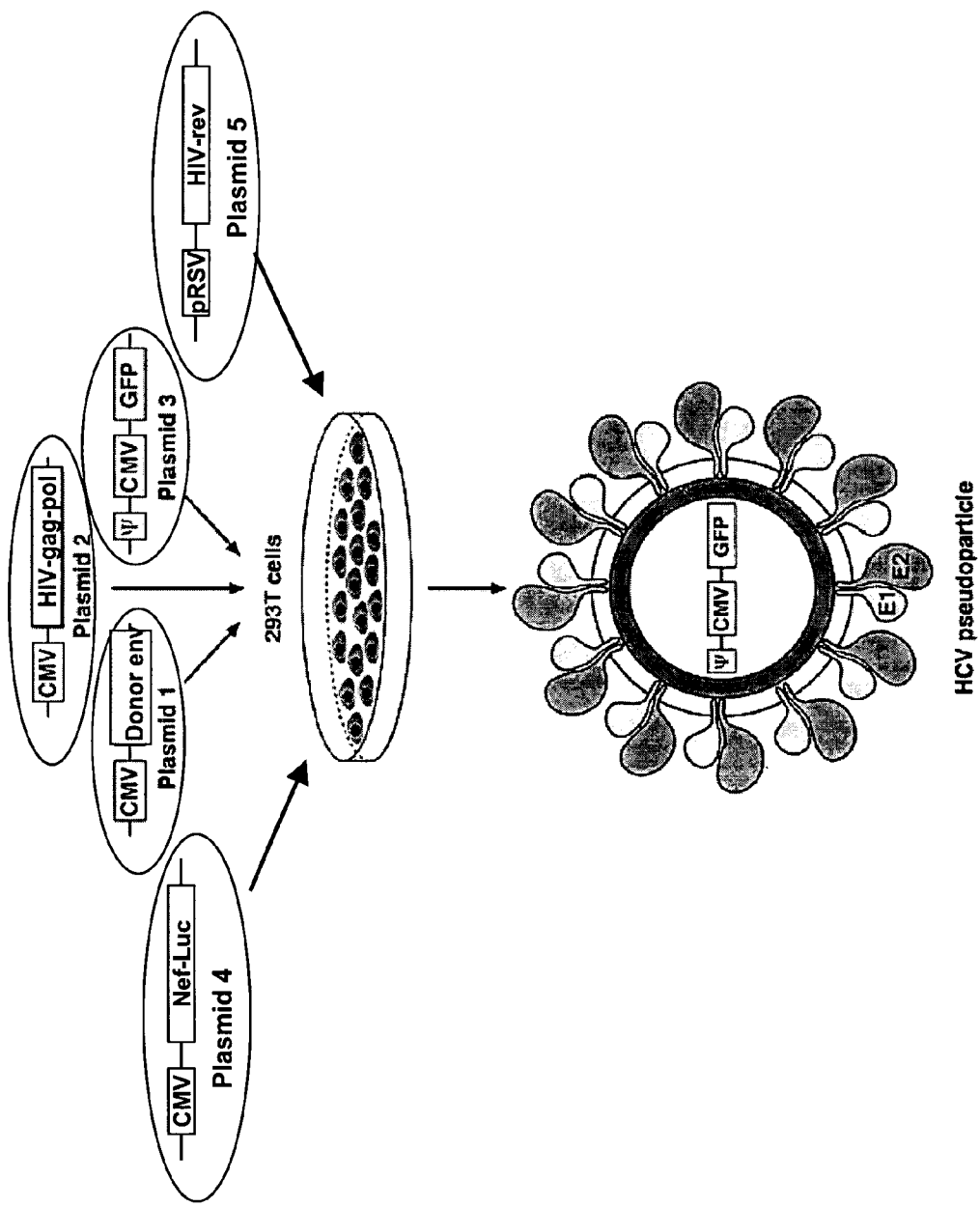
FIG. 12 shows the production of pseudotyped virus comprising HIV Nef-Luc fusion protein.

To produce pseudotyped virus comprising HIV Nef-Luc fusion protein, 293FT cells were transfected with plasmid constructs shown in FIG. 12. These encoded the HIV gag-pol, HIV rev, the viral envelope protein of interest and an HIV packageable marker gene ($y_{HIV}$-b-galactosidase or $y_{HIV}$-GFP). Transfected cells were cultured for 48 h and then cell culture supernatant as collected. The supernatant was filtered through a 0.45 micron filter, followed by ultracentrifugation through a 20% sucrose cushion. Virus pellet was resuspended in DMEM+10% FBS (usually in a volume 100-fold less than the starting volume). Purified env pseudotyped particles containing the recombinant nef-luciferase fusion protein were then stored at −70° C. until used.

Vesicular Stomatitis Virus (VSV) Or Rabies Env Pseudotyped Viruses

Figure 13:
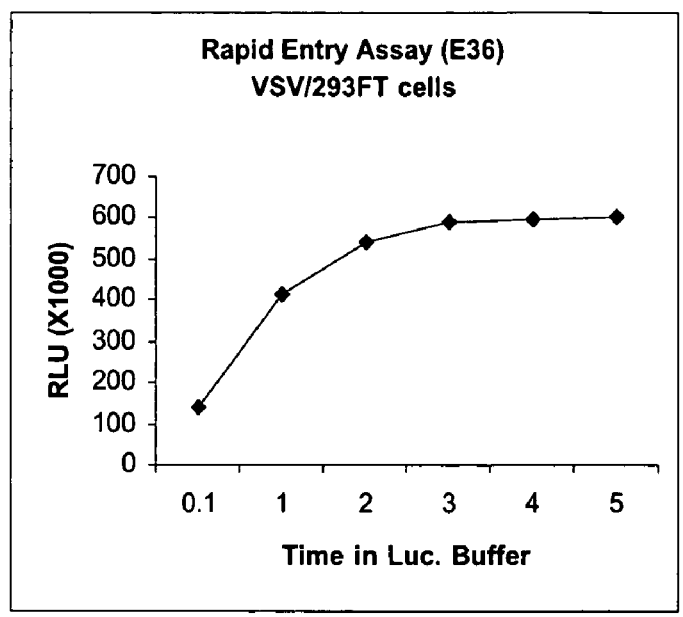
FIG. 13 shows the results of viral entry assay using VSV env pseudotyped viruses expressing HIV Nef-Luc fusion protein. Approximately $10^6$ 293FT cells were resuspended with 0.2 ml of sucrose-purified VSV pseudoparticle and incubated at 37° C. for 3 h with continuous rotation. At the end of incubation, the cells were pelleted, washed with DMEM+10% FBS and resuspended in luciferin-containing buffer (Promega). Luciferase activity was measured immediately after the addition of buffer, and then at 1 min. intervals for 5 min.
Figure 14:
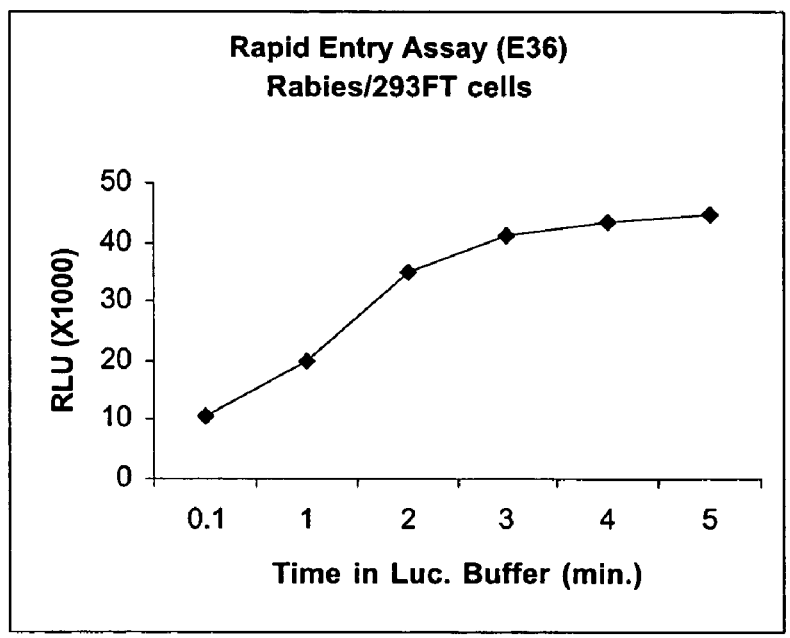
FIG. 14 shows the results of viral entry assay using Rabies env pseudotyped viruses expressing HIV Nef-Luc fusion protein. Approximatley $10^6$ 293FT cells were resuspended with 0.2 ml of sucrose-purified rabies pseudoparticle and incubated at 37° C. for 3 h with continuous rotation. At the end of incubation, the cells were washed with DMEM+10% FBS and resuspended in luciferase buffer (Promega). Luciferase activity was measured immediately after the addition of luciferase buffer, and then at 1 minute intervals for 5 minutes
Figure 15:
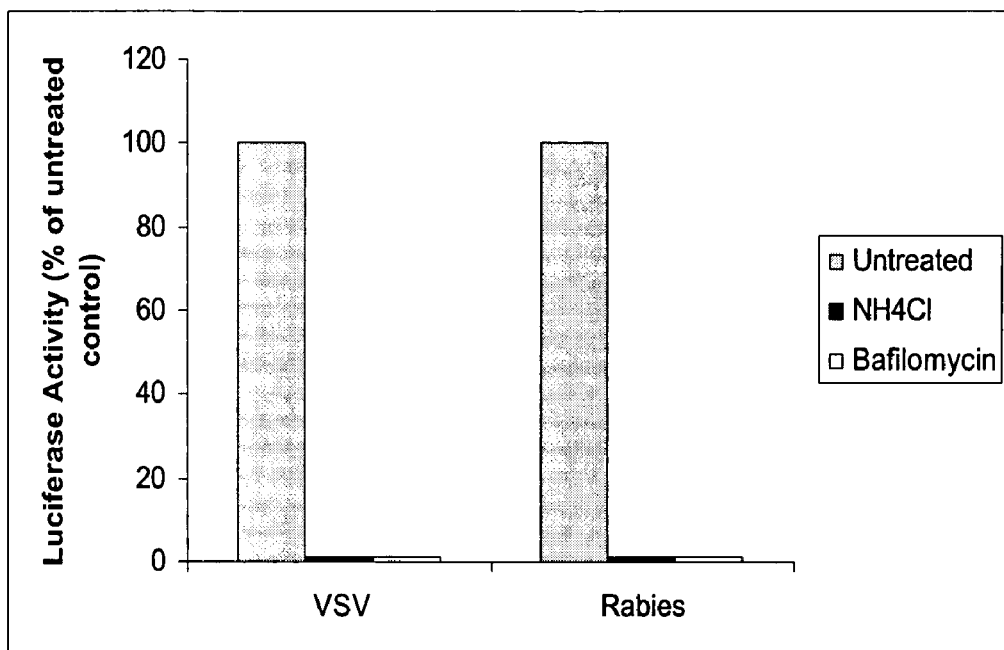
FIG. 15 shows the effect of endosomal acidification inhibitors on the entry of VSV and Rabies env pseudotyped viruses expressing HIV Nef-Luc fusion protein. 293FT cells were trypsinized and $10^6$ cells were pre-treated with NH4Cl (20 mM) or Bafilomycin (40 nM) for 1 hour, followed by incubation with sucrose-purified env pseudotyped virus (VSV or Rabies) for 1 hour. Subsequently, the cells were washed and luciferase activity was measured.

FIGS. 13 and 14 show the results of viral entry assays using vesicular stomatitis virus or rabies env pseudotyped viruses expressing HIV Nef-Luc fusion protein. VSV and Rabies virus belong to the family Rhabdoviridae. Members of this family are known to enter the cell through a pH-dependent endosomal pathway. Use of agents, such as $NH_4Cl$ and bafilomycin, which inhibit the endosomal acidification are known to impair the entry of these viruses by inhibiting fusion of viral and cellular vesicular membrane. Therefore, to test if the rapid entry assay gives a valid measure of virus entry, the effects of endosomal acidification inhibitors on the entry of the VSV or rabies env pseudotyped viruses were examined. FIG. 15 shows that $NH_4Cl$ and bafilomycin completely inhibit luciferase activities in the viral entry assay.

Murine Leukemia Virus (MLV) Env Pseudotyped Viruses

Figure 16:
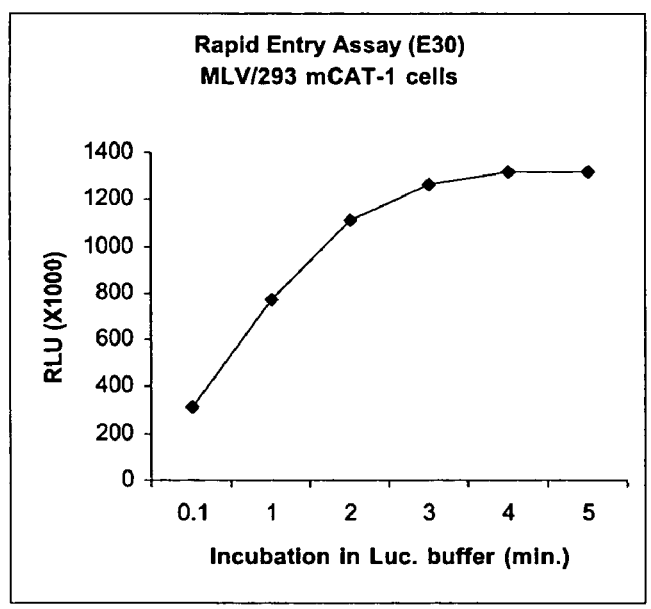
FIG. 16 shows the results of viral entry assay using murine leukemia virus (MLV) env pseudotyped viruses expressing HIV Nef-Luc fusion protein. Approximately $10^6$ 293-mCAT-1 cells were incubated with 0.2 ml of sucrose-purified MLV env pseudotyped virus at 37° C. for 3 h with continuous rotation. At the end of incubation, the cells were pelleted, washed with DMEM+10% FBS and resuspended in luciferin-containing buffer (Promega). Luciferase activity was measured immediately after adding the luciferase buffer and then at 1 min. intervals for 5 min.
Figures 17, 18:
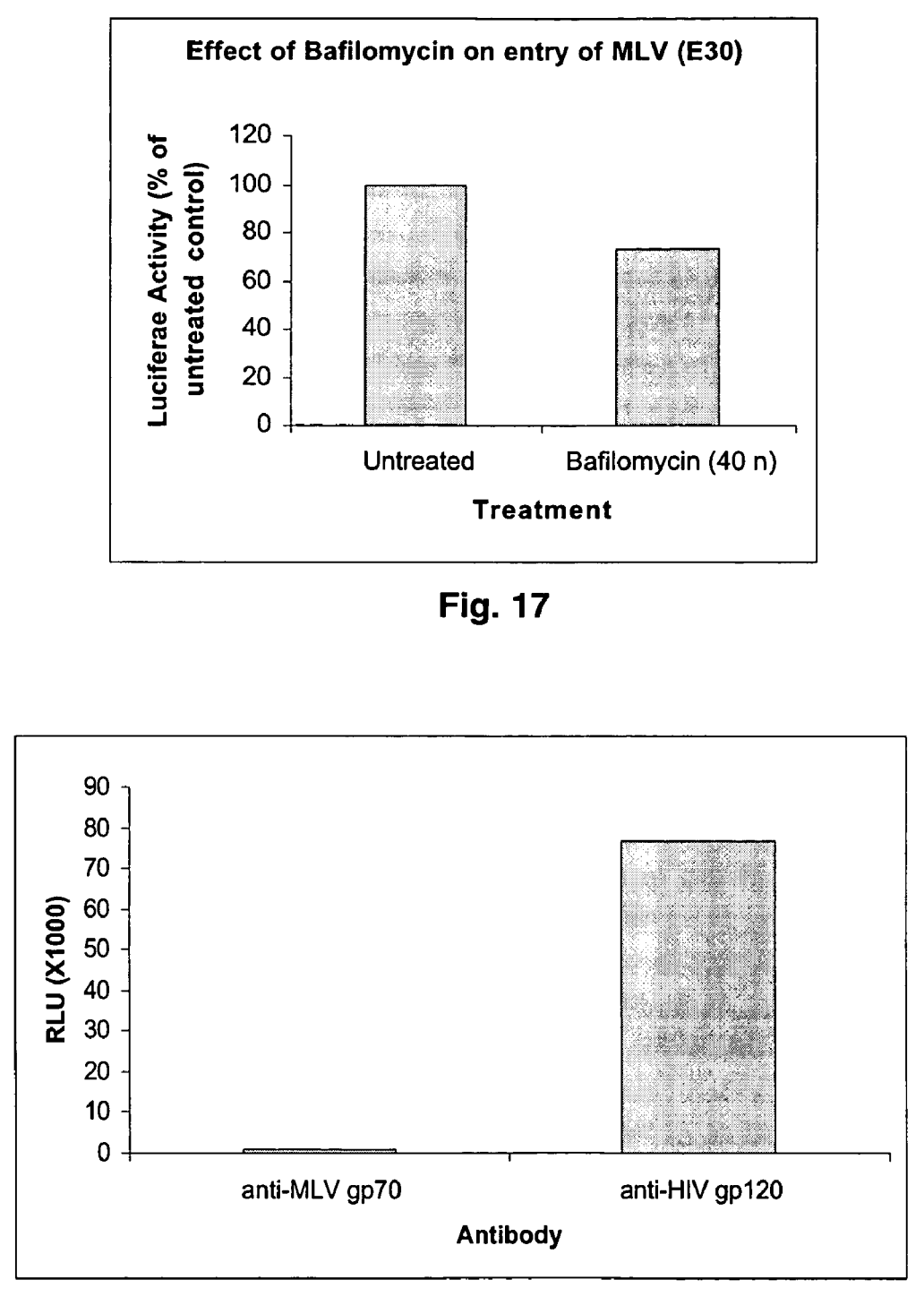

FIG. 16 shows the results of viral entry assays using murine leukemia virus env pseudotyped viruses expressing HIV Nef-Luc fusion protein. Unlike VSV and Rabies virus, fusion of MLV is pH-independent. To determine the effect of bafilomycin (an inhibitor of endosomal acidification) on entry of MLV env pseudotyped particles, 293 mCAT-1 cells were trypsinized and approx. $10^6$ cells were pre-incubated with or without bafilomycin (40 nM) for 1 h at 37° C. Subsequently, sucrose-purified MLV env pseudotyped virus were added and incubation continued for an additional hour. The cells were then washed and luciferase activity was measured. FIG. 17 shows that treatment with bafilomycin had little effect on luciferase activities in the viral entry assay.

Virus neutralization by specific antibodies is well accepted as a specific diagnostic assay. To demonstrate the use of the entry assay as a valid diagnostic tool, the effect of specific antibodies was tested on the entry of MLV pseudotype. HEK 293mCAT-1 cells were trypsinized and approx. $10^6$ cells were incubated with sucrose-purified MLV env pseudotyped virus, which were previously incubated with either anti-MLVgp70 antibody or anti-HIVgp120. Incubation was carried out for 3 h at 37° C. with continuous rotation. Subsequently, the cells were pelleted, washed with DMEM+10% FBS and resuspended in luciferin-containing buffer. Luciferase activity was measured 2 minutes after the addition of buffer. A very weak luciferase signal was detected in cells that were incubated with anti-MLVgp70-treated MLV pseudotype (FIG. 18). In contrast, very high luciferase counts were obtained in cells incubated with anti-HIVgp120-treated MLV pseudotype. These results clearly demonstrate that the entry assay could potentially be used as a highly specific serodiagnostic tool.

Ebola Env Pseudotyped Viruses

Figures 19, 20:
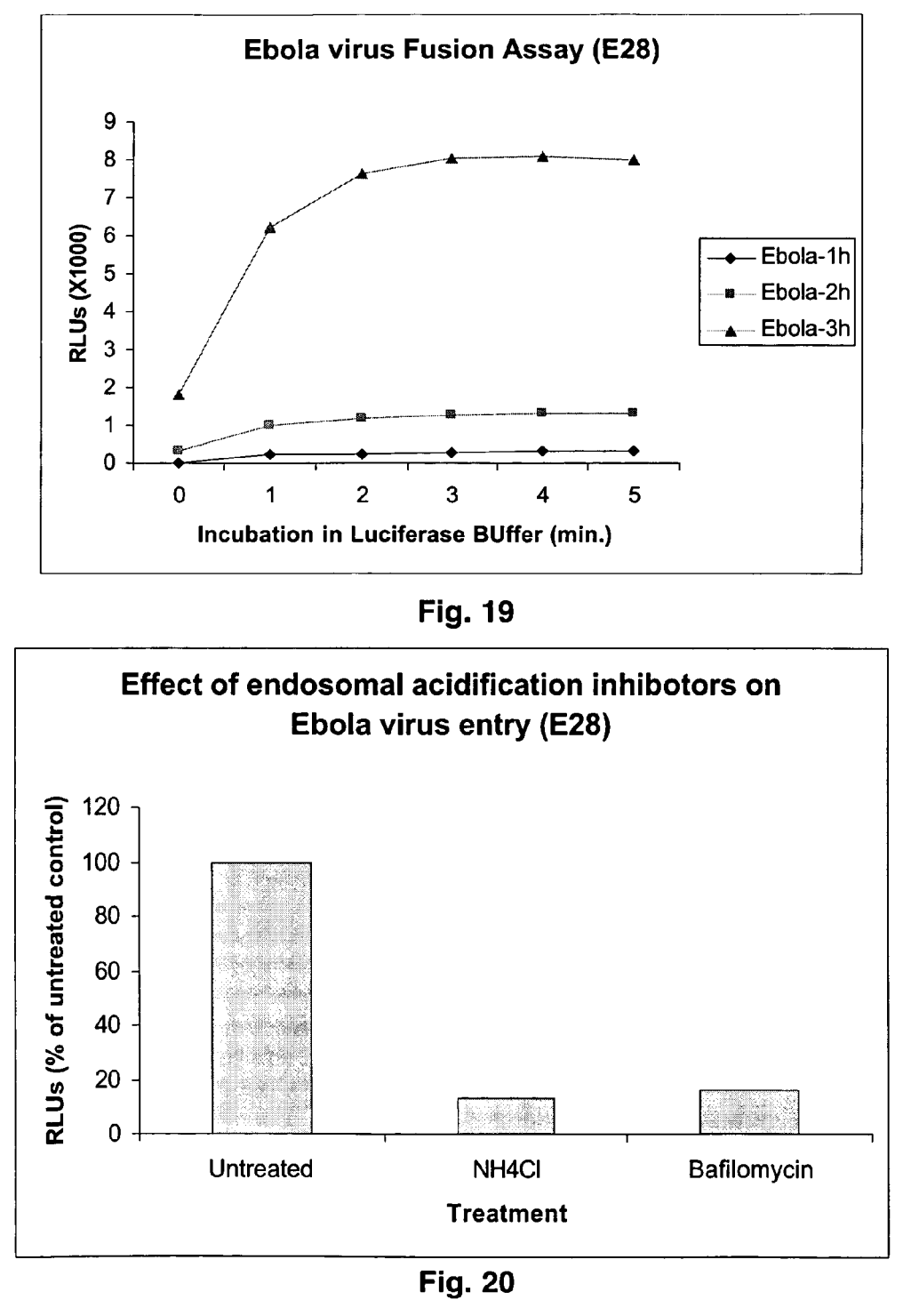

FIG. 19 shows entry kinetics of Ebola env pseudotyped viruses expressing HIV Nef-Luc fusion protein. HEK293FT cells were trypsinized and approx. $10^6$ cells were incubated with sucrose-purified Ebola env pseudotyped particles for 1, 2 or 3 h. At the end of each incubation period, the cells were pelleted, washed once with DMEM+10% FBS and resuspended in luciferin-containing buffer. Luciferase activity was measured immediately after resuspension, and then at 1 min. intervals for 5 min.

Figures 21, 22:
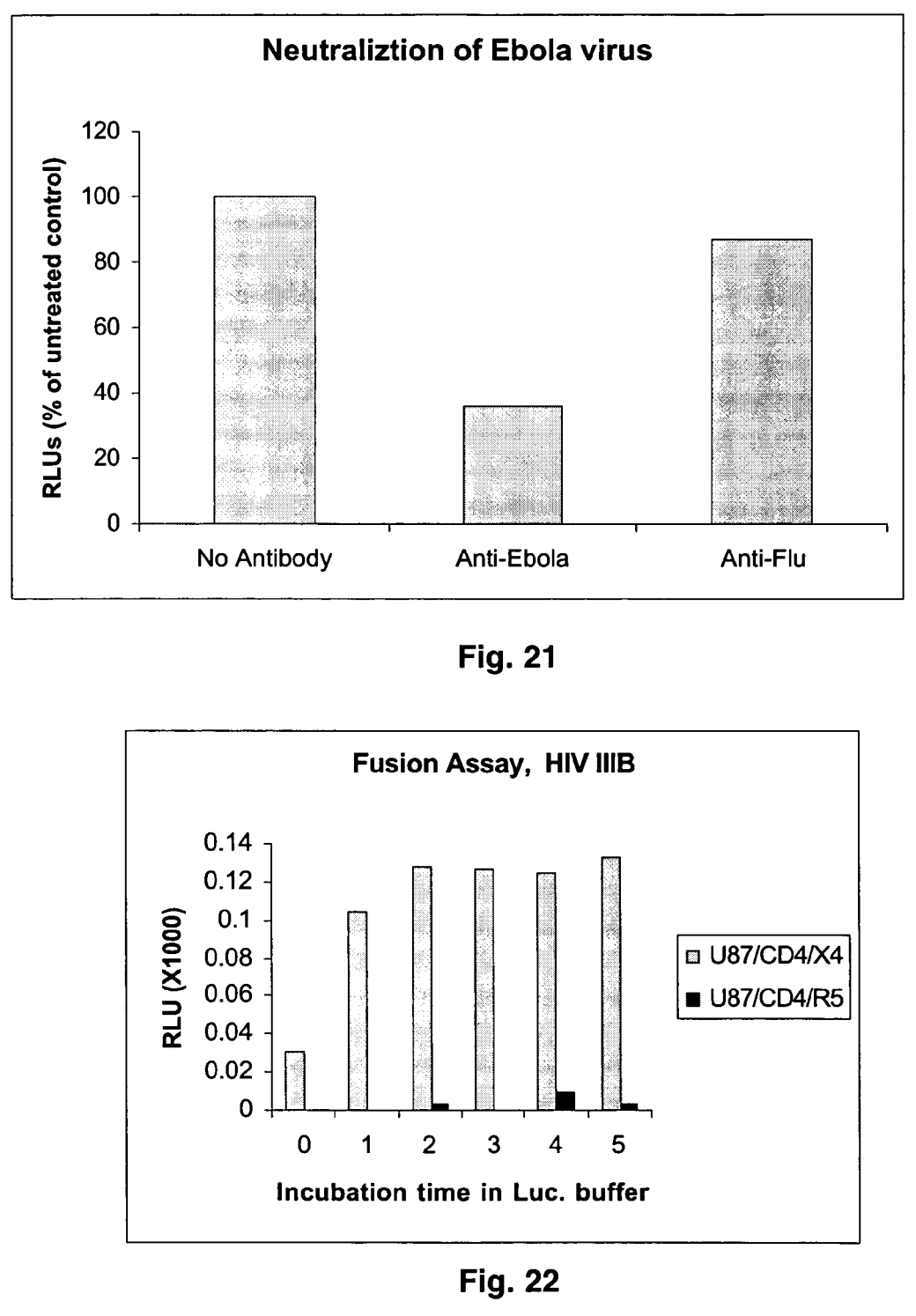

It has been demonstrated that entry of wild-type Ebola virus is sensitive to inhibitors of endosomal acidification. To demonstrate that similar results are obtained by rapid entry assay, HEK 293FT cells were trypsinized and approx. $10^6$ cells were pretreated with $NH_4Cl$ (20 mM) or bafilomycin (40 nM) for 1 h at 37° C. Subsequently, sucrose-purified Ebola virus env pseudotyped virus were added to each sample and incubation continued for an additional 3 h. Cells were then pelleted, washed once with DMEM+10% FBS and resuspended in luciferase buffer. Luciferase activity was measured 2 min. after resuspension. Results shown in FIG. 20 show that entry of Ebola virus env pseudotyped particles was significantly inhibited by endosomal acidification inhibitors, thus indicating that rapid entry assay measures true fusion and entry events as those of wild-type Ebola virus. FIG. 21 shows viral entry of Ebola virus env pseudotyped virus was significantly inhibited by Ebola virus-specific antibodies. Anti-Ebola antibody substantially (~65%) reduced the luciferase signal, while anti-influenza antibody had no significant effect as compared to the control untreated sample.

HIV-1 Env Pseudotyped Virus

Entry of HIV-1 into target cells is dependent on the availability of receptor (CD4) and co-receptor (CXCR4 or CCR5) on the surface of target cells. Based on co-receptor specificity, HIV-1 has been classified into two strains: (i) those that infect cells bearing CXCR4 co-receptor, but not cells bearing CCR5; and (ii) those that infect cells bearing CCR5 co-receptor, but not cells bearing CXCR4. For the following rapid entry assays, gp160 (HIV envelope protein) from HIV IIIB strain (CXCR4-tropic strain) and HIV JFRL strain (CCR5-tropic strain) were used. Using these two different envelope proteins, HIV-1 env pseudotyped virus were generated and fusion assay was performed using U87 glioblastoma cells transfected with either CD4+CXCR4 (U87/CD4/X4) or CD4+CCR5 (U87/CD4/R5). A semi confluent plate of each cell type was trypsinized and approx $8\times10^5$ cells of each type were incubated with sucrose-purified HIV IIIB-based env pseudotyped virus or sucrose purified HIV-JFRL-based env pseudotyped virus for 5 h at 37° C. with continuous rotation. After the incubation, cells were pelleted, washed once with DMEM+10% FBS, and resuspended in luciferin-containing buffer. Luciferase activity was measured immediately after the addition of buffer, and then at 1 min. intervals for 5 min. FIGS. 22 and 23 show that these env pseudotyped virus exhibit the same cellular tropism as that of wild type HIV.

T-20 peptide (ENFURVITIDE) is a recently approved drug for the treatment of HIV patients. T-20 targets the entry of HV-1. It interacts with a specific region in the viral gp41 HIV envelope protein subunit that mediates entry and inhibits fusion between viral and cellular membranes. Since the entry assay disclosed herein could be used as a tool to screen entry inhibitors, the sensitivity of this assay to the T-20 peptide was tested.

U87 cells bearing CD4 and CCR5 (U87/CD4/R5) were trypsinized and approx. $8\times10^5$ cells were incubated with T-20 peptide at various concentrations (0, 1000, 500, 250 and 125 ng/ml) for 1 h at 37° C. with continuous rotation. After the incubation, the cells were pelleted and resuspended with purified HIV-JFRL envelope protein pseudotyped particles (0.2 ml). Each reaction was replenished with the same concentration of T-20 peptide as before. The tubes were incubated for an additional 5 h, followed by washing of cells with DMEM+10% FBS. The washed pellets were then resuspended in luciferin-containing buffer. Luciferase activity was measured 2 min. after the addition of buffer. Luciferase activity in T-20-treated samples was compared to that in untreated sample and % inhibition was determined. Results in FIG. 24 show that the T-20 peptide inhibit luciferase activity (and viral entry) in a dose dependent manner.

What is claimed is:

1. A method of detecting virus binding and entry to a target cell, said method comprising the steps of:
    attaching an enzyme to the C-terminal end of a viral envelope protein, wherein the C-terminal end of the viral envelope protein is located on the inner side of the viral membrane, thereby creating an envelope-enzyme fusion protein;
    generating virus particles comprising said fusion protein and wild type viral envelope protein, wherein the enzyme of the envelope-enzyme fusion protein is encapsidated in the virus particles;
    infecting target cells with the virus particles; and
    measuring activities of the enzyme in infected cells, wherein the activities measured are the activities of the enzyme incorporated into the virus itself,
    wherein levels of enzyme activities are measures of virus binding and entry to the target cells mediated by the wild type envelope protein.

2. The method of claim 1, further comprising:
    evaluating the effect of amino acid substitutions on virus binding and entry.

3. The method of claim 2, wherein said evaluating step comprises:
    constructing a mutant viral envelope protein comprising amino acid substitution(s);
    attaching an enzyme to the C-terminal end of the mutant viral envelope protein, thereby creating an envelope-enzyme fusion protein;
    generating virus particles comprising the fusion protein and a wild type viral envelope protein, wherein the enzyme of the envelope-enzyme fusion protein is encapsidated in the virus particles;
    infecting target cells with the virus particles;
    measuring activities of the enzyme in lysed and intact infected cells; and
    comparing levels of the enzyme activities with those in the cells infected with virus comprising the fusion protein and the wild type envelope protein, thereby evaluating the influence of amino acid substitutions on virus binding and entry.

4. The method of claim 1, further comprising:
    determining whether a viral entry mechanism is pH dependent.

5. The method of claim 4, wherein said determining step comprises:
    measuring activities of the enzyme in the infected cells in the presence and absence of inhibitors of endosomal acidification, wherein decreased enzyme activities in the presence of the inhibitors indicates that the virus has a pH-dependent mode of entry.

6. The method of claim 1, further comprising:
    screening for neutralizing antibodies in a serum sample.

7. The method of claim 6, wherein said screening step comprises:
    measuring activities of the enzyme in the infected cells in the presence or absence of the serum sample, wherein decreased enzyme activities in the presence of the serum indicates the serum contains neutralizing antibodies that inhibit viral entry and binding mediated by the wild type viral envelope protein.

8. The method of claim 1, further comprising:
    screening for compound that inhibits virus binding and entry to the target cell.

9. The method of claim 8, further comprising:
    infecting the target cells with the virus particles in the presence or absence of the compound; and
    measuring activities of the enzyme in the infected cells, wherein decreased enzyme activities in the presence of the compound indicates that the compound inhibits virus binding and entry mediated by the wild type viral envelope protein.

10. The method of claim 1, wherein the enzyme is luciferase.

11. The method of claim 1, wherein the fusion protein comprises envelope protein of murine leukemia virus or Nef protein.

12. The method of claim 1, wherein the wild type viral envelope protein is from a virus selected from the group consisting of murine leukemia virus, human immunodeficiency virus, retrovirus, Vesicular Stomatitis virus, Arenaviruses, Hanta virus, Ebola virus and Venezuelan Equine Encephalitis virus.

13. The method of claim 1, wherein measurement of enzyme activities is carried out in 96-well plate.

* * * * *